United States Patent
Al-Ghamdi

(10) Patent No.: US 11,066,611 B2
(45) Date of Patent: Jul. 20, 2021

(54) SYSTEM FOR CONVERSION OF CRUDE OIL TO PETROCHEMICALS AND FUEL PRODUCTS INTEGRATING VACUUM GAS OIL HYDROTREATING AND STEAM CRACKING

(71) Applicant: Saudi Arabian Oil Company, Dhahran (SA)

(72) Inventor: Mohammed Saeed Al-Ghamdi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 110 days.

(21) Appl. No.: 16/568,774

(22) Filed: Sep. 12, 2019

(65) Prior Publication Data
US 2021/0079305 A1   Mar. 18, 2021

Related U.S. Application Data

(63) Continuation of application No. 15/817,127, filed on Nov. 17, 2017, now Pat. No. 10,619,112.
(Continued)

(51) Int. Cl.
*C10G 69/00*   (2006.01)
*B01J 19/24*   (2006.01)
(Continued)

(52) U.S. Cl.
CPC ............... *C10G 69/00* (2013.01); *B01D 3/10* (2013.01); *B01D 3/143* (2013.01); *B01D 3/40* (2013.01); *B01J 19/2445* (2013.01); *C07C 6/10* (2013.01); *C07C 29/04* (2013.01); *C10L 1/08* (2013.01); *C10G 2300/1044* (2013.01); *C10G 2300/1048* (2013.01); *C10G 2300/1059* (2013.01); *C10G 2300/1077* (2013.01);
(Continued)

(58) Field of Classification Search
CPC ........ C10G 69/00; C10G 69/06; C10G 69/14; C07C 6/04; C07C 6/10; B01J 19/2445; B01J 19/245

See application file for complete search history.

(56) References Cited

U.S. PATENT DOCUMENTS

| 3,472,909 A | 10/1969 | Raymond |
| 3,702,292 A | 11/1972 | Burich |

(Continued)

*Primary Examiner* — Lessanework Seifu
(74) *Attorney, Agent, or Firm* — Abelman, Frayne and Schwab

(57) ABSTRACT

Process scheme configurations are disclosed that enable conversion of crude oil feeds with several processing units in an integrated manner into petrochemicals. The designs utilize minimum capital expenditures to prepare suitable feedstocks for the steam cracker complex. The integrated process for converting crude oil to petrochemical products including olefins and aromatics, and fuel products, includes mixed feed steam cracking and gas oil steam cracking. Feeds to the mixed feed steam cracker include light products and naphtha from hydroprocessing zones within the battery limits, recycle streams from the C3 and C4 olefins recovery steps, and raffinate from a pyrolysis gasoline aromatics extraction zone within the battery limits. Feeds to the gas oil steam cracker include hydrotreated gas oil range intermediates from vacuum gas oil hydrotreating.

13 Claims, 11 Drawing Sheets

Related U.S. Application Data

(60) Provisional application No. 62/424,883, filed on Nov. 21, 2016, provisional application No. 62/450,018, filed on Jan. 24, 2017, provisional application No. 62/450,024, filed on Jan. 24, 2017, provisional application No. 62/450,043, filed on Jan. 24, 2017, provisional application No. 62/450,062, filed on Jan. 24, 2017.

(51) Int. Cl.
*C07C 29/04* (2006.01)
*C07C 6/10* (2006.01)
*B01D 3/10* (2006.01)
*B01D 3/14* (2006.01)
*B01D 3/40* (2006.01)
*C10L 1/08* (2006.01)

(52) U.S. Cl.
CPC . *C10G 2300/1081* (2013.01); *C10G 2400/04* (2013.01); *C10G 2400/08* (2013.01); *C10G 2400/20* (2013.01); *C10G 2400/30* (2013.01); *C10L 2200/043* (2013.01); *C10L 2200/0446* (2013.01); *C10L 2270/026* (2013.01); *C10L 2270/04* (2013.01); *C10L 2290/543* (2013.01)

(56) References Cited

U.S. PATENT DOCUMENTS

| | | | |
|---|---|---|---|
| 3,842,138 A | 10/1974 | Chahvekilian et al. |
| 3,855,113 A | 12/1974 | Gould |
| 3,898,299 A | 8/1975 | Jones |
| 4,065,379 A | 12/1977 | Soonawala et al. |
| 4,115,467 A | 9/1978 | Fowler |
| 4,180,453 A | 12/1979 | Franck et al. |
| 5,906,728 A | 5/1999 | Iaccino et al. |
| 5,980,732 A | 11/1999 | Gillis |
| 5,981,818 A | 11/1999 | Purvis et al. |
| 6,166,279 A | 12/2000 | Schwab et al. |
| 6,210,561 B1 | 4/2001 | Bradow et al. |
| 6,538,168 B1 | 3/2003 | Schwab et al. |
| 7,550,642 B2 | 6/2009 | Powers |
| 7,938,952 B2 | 5/2011 | Coylar et al. |
| 8,394,900 B2 | 3/2013 | Abhari |
| 8,529,753 B2 | 9/2013 | Niu et al. |
| 8,540,870 B2 | 9/2013 | McGehee et al. |
| 8,722,950 B2 | 5/2014 | Hal et al. |
| 8,754,277 B2 | 6/2014 | Vijayakumari et al. |
| 8,936,716 B2 | 1/2015 | Hoehn et al. |
| 8,940,950 B2 | 1/2015 | Ellrich et al. |
| 9,273,256 B2 | 3/2016 | Gillis et al. |
| 9,452,955 B2 | 9/2016 | Sieli et al. |
| 9,464,240 B2 | 10/2016 | Bridges et al. |
| 9,550,707 B2 | 1/2017 | Schrod et al. |
| 9,650,580 B2 | 5/2017 | Merdrignac et al. |
| 9,856,425 B2 | 1/2018 | Ward et al. |
| 9,862,898 B2 | 1/2018 | Ward et al. |
| 9,920,263 B2 | 3/2018 | Klein et al. |
| 2004/0054247 A1 | 3/2004 | Powers |
| 2007/0090018 A1 | 4/2007 | Keusenkothen et al. |
| 2007/0232846 A1 | 10/2007 | Baumgartner et al. |
| 2008/0194900 A1 | 8/2008 | Bhirud |
| 2010/0056839 A1 | 3/2010 | Ramachandran et al. |
| 2010/0087692 A1 | 4/2010 | Yoshimura et al. |
| 2010/0168487 A1 | 7/2010 | Sawyer et al. |
| 2010/0285950 A1 | 11/2010 | Mao |
| 2011/0042269 A1 | 2/2011 | Keuchler et al. |
| 2011/0119994 A1 | 5/2011 | Hogendoorn et al. |
| 2011/0174682 A1 | 7/2011 | Iaccino |
| 2013/0237714 A1 | 9/2013 | Vijayakumari et al. |
| 2013/0245295 A1 | 9/2013 | Westrenen |
| 2013/0248419 A1 | 9/2013 | Abba et al. |
| 2014/0081061 A1 | 3/2014 | Stanley et al. |
| 2016/0115400 A1 | 4/2016 | Sun et al. |
| 2016/0137933 A1 | 5/2016 | Ward et al. |
| 2016/0368838 A1 | 12/2016 | Ward et al. |
| 2016/0369180 A1 | 12/2016 | Ward et al. |
| 2016/0369188 A1 | 12/2016 | Housmans et al. |
| 2016/0369190 A1 | 12/2016 | Ward et al. |
| 2017/0009155 A1 | 1/2017 | Oprins |
| 2018/0142168 A1* | 5/2018 | Al-Ghamdi ............ C10G 69/06 |

\* cited by examiner

SYSTEM FOR CONVERSION OF CRUDE OIL TO PETROCHEMICALS AND FUEL PRODUCTS INTEGRATING VACUUM GAS OIL HYDROTREATING AND STEAM CRACKING

RELATED APPLICATIONS

This application is a Continuation of U.S. patent application Ser. No. 15/817,127 filed Nov. 17, 2017, which claims priority to U.S. Provisional Patent Application No. 62/424,883 filed Nov. 21, 2016, U.S. Provisional Patent Application No. 62/450,018 filed Jan. 24, 2017, U.S. Provisional Patent Application No. 62/450,024 filed Jan. 24, 2017, U.S. Provisional Patent Application No. 62/450,043 filed Jan. 24, 2017, and U.S. Provisional Patent Application No. 62/450,062 filed Jan. 24, 2017, the contents of which are all incorporated herein by reference in their entireties.

BACKGROUND OF THE INVENTION

Field of the Invention

The inventions disclosed herein relate to an integrated process and system for converting crude oil to petrochemicals and fuel products.

Description of Related Art

The lower olefins (i.e., ethylene, propylene, butylene and butadiene) and aromatics (i.e., benzene, toluene and xylene) are basic intermediates which are widely used in the petrochemical and chemical industries. Thermal cracking, or steam pyrolysis, is a major type of process for forming these materials, typically in the presence of steam, and in the absence of oxygen. Typical feedstocks for steam pyrolysis can include petroleum gases, such as ethane, and distillates such as naphtha, kerosene and gas oil. The availability of these feedstocks is usually limited and requires costly and energy-intensive process steps in a crude oil refinery.

A very significant portion of ethylene production relies on naphtha as the feedstock. However, heavy naphtha has a lower paraffin and higher aromatics content than light naphtha, making it less suitable as feedstock in the production of ethylene without upgrading. Heavy naphtha can vary in the amount of total paraffins and aromatics based on its source. Paraffins content can range between about 27-70%, naphthenes content can range between about 15-60%, and the aromatics content can range between about 10-36% (volume basis).

Many chemicals producers are limited by the supply and quality of feed from nearby refiners due to reliance on oil refinery by-products as feed. Chemicals producers are also limited by the high cost of oil refining and its associated fuels markets, which may negatively influence the economic value of refinery sourced feeds. Higher global fuel efficiency standards for automobiles and trucks will reduce fuels demand and narrow refinery margins, and may complicate the economics of fuels and chemicals supply and/or markets.

A need remains in the art for improved processes for converting crude oil to basic chemical intermediates such as lower olefins and aromatics. In addition, a need remains in the art for new approaches that offer higher value chemical production opportunities with greater leverage on economies of scale.

SUMMARY

In accordance with one or more embodiments, the invention relates to an integrated process for producing petrochemicals and fuel product from a crude oil feed. The integrated process includes an initial separation step to separate from a crude oil feed in an atmospheric distillation zone at least a fraction comprising straight run naphtha and lighter components, one or more middle distillate fractions, and an atmospheric residue fraction. A vacuum gas oil fraction is separated from the atmospheric residue fraction in a vacuum distillation zone. In a distillate hydroprocessing ("DHP") zone, such as a diesel hydrotreater, at least a portion of the middle distillates are processed to produce a naphtha fraction and a diesel fuel fraction. The vacuum gas oil fraction (and optionally all or a portion of an atmospheric gas oil fraction, or all or a portion of a heavy atmospheric gas oil fraction) is processed in a gas oil hydrotreating zone, and the hydrotreated effluents are processed in a gas oil steam cracking zone. The fraction(s) from the atmospheric distillation with straight run naphtha and lighter components, and an aromatics extraction zone raffinate, are processed in a mixed feed steam cracking zone. The products from the mixed feed steam cracking zone and the gas oil steam cracking zone include integrated or separate mixed product stream(s) comprising $H_2$, methane, ethane, ethylene, mixed C3s and mixed C4s; pyrolysis gasoline stream(s); and pyrolysis oil stream(s).

From the mixed product stream(s) C3s and the mixed C4s, petrochemicals ethylene, propylene and butylenes are recovered. Ethane and non-olefinic C3s are recycled to the mixed feed steam cracking zone, and non-olefinic C4s are recycled to the mixed feed steam cracking zone or to a separate processing zone for production of additional petrochemicals. Pyrolysis gasoline is treated in a py-gas hydroprocessing zone to produce hydrotreated pyrolysis gasoline. The hydrotreated pyrolysis gasoline is routed to the aromatics extraction zone to recover aromatic products and the aromatics extraction zone raffinate that is recycled to the mixed feed steam cracking zone.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

The invention will be described in further detail below and with reference to the attached drawings in which the same or similar elements are referred to by the same number, and where.

DESCRIPTION

Figure 1:
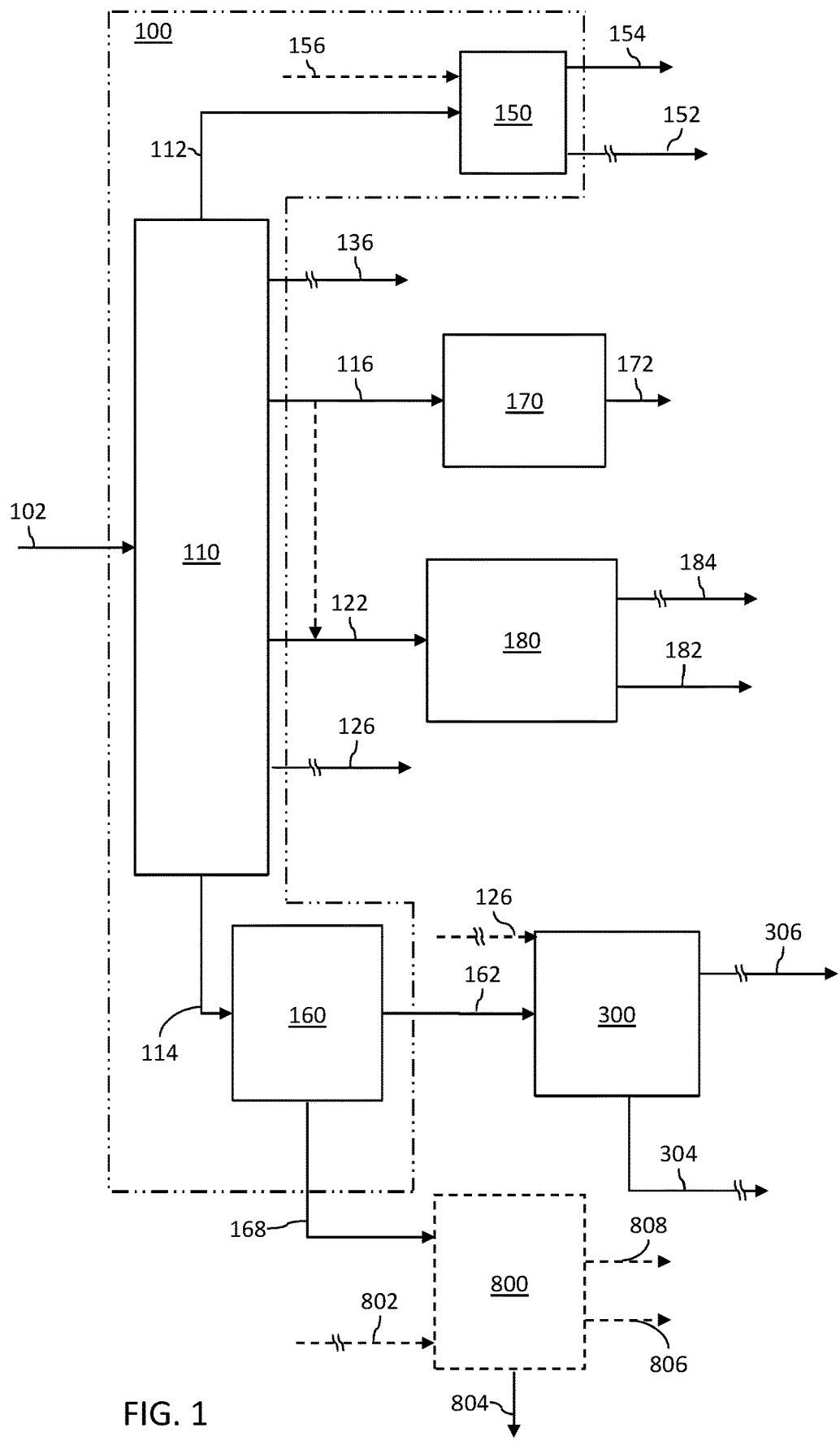
FIG. 1 schematically depicts operations upstream of a steam cracker complex in embodiments of processes for producing petrochemicals and fuel product.

Process scheme configurations are disclosed that enable conversion of crude oil feeds with several processing units in an integrated manner into petrochemicals. The designs utilize minimum capital expenditures to prepare suitable feedstocks for the steam cracker complex. The integrated process for converting crude oil to petrochemical products including olefins and aromatics, and fuel products, includes mixed feed steam cracking and gas oil steam cracking. Feeds to the mixed feed steam cracker include light products and naphtha from hydroprocessing zones within the battery limits, recycle streams from the C3 and C4 olefins recovery steps, and raffinate from a pyrolysis gasoline aromatics extraction zone within the battery limits. Feeds to the gas oil steam cracker include hydrotreated gas oil range intermediates from vacuum gas oil hydrotreating.

The phrase "a major portion" with respect to a particular stream or plural streams means at least about 50 wt % and up to 100 wt %, or the same values of another specified unit.

The phrase "a significant portion" with respect to a particular stream or plural streams means at least about 75 wt % and up to 100 wt %, or the same values of another specified unit.

The phrase "a substantial portion" with respect to a particular stream or plural streams means at least about 90, 95, 98 or 99 wt % and up to 100 wt %, or the same values of another specified unit.

The phrase "a minor portion" with respect to a particular stream or plural streams means from about 1, 2, 4 or 10 wt %, up to about 20, 30, 40 or 50 wt %, or the same values of another specified unit.

The term "crude oil" as used herein refers to petroleum extracted from geologic formations in its unrefined form. Crude oil suitable as the source material for the processes herein include Arabian Heavy, Arabian Light, Arabian Extra Light, other Gulf crudes, Brent, North Sea crudes, North and West African crudes, Indonesian, Chinese crudes, or mixtures thereof. The crude petroleum mixtures can be whole range crude oil or topped crude oil. As used herein, "crude oil" also refers to such mixtures that have undergone some pre-treatment such as water-oil separation; and/or gas-oil separation; and/or desalting; and/or stabilization. In certain embodiments, crude oil refers to any of such mixtures having an API gravity (ASTM D287 standard), of greater than or equal to about 20°, 30°, 32°, 34°, 36°, 38°, 40°, 42° or 44°.

The acronym "AXL" as used herein refers to Arab Extra Light crude oil, characterized by an API gravity of greater than or equal to about 38°, 40°, 42° or 44°, and in certain embodiments in the range of about 38°-46°, 38°-44°, 38°-42°, 38°-40.5°, 39°-46°, 39°-44°, 39°-42° or 39°-40.5°.

The acronym "AL" as used herein refers to Arab Light crude oil, characterized by an API gravity of greater than or equal to about 30°, 32°, 34°, 36° or 38°, and in certain embodiments in the range of about 30°-38°, 30°-36°, 30°-35°, 32°-38°, 32°-36°, 32°-35°, 33°-38°, 33°-36° or 33°-35°.

The acronym "LPG" as used herein refers to the well-known acronym for the term "liquefied petroleum gas," and generally is a mixture of C3-C4 hydrocarbons. In certain embodiments, these are also referred to as "light ends."

The term "naphtha" as used herein refers to hydrocarbons boiling in the range of about 20-205, 20-193, 20-190, 20-180, 20-170, 32-205, 32-193, 32-190, 32-180, 32-170, 36-205, 36-193, 36-190, 36-180 or 36-170° C.

The term "light naphtha" as used herein refers to hydrocarbons boiling in the range of about 20-110, 20-100, 20-90, 20-88, 32-110, 32-100, 32-90, 32-88, 36-110, 36-100, 36-90 or 36-88° C.

The term "heavy naphtha" as used herein refers to hydrocarbons boiling in the range of about 90-205, 90-193, 90-190, 90-180, 90-170, 93-205, 93-193, 93-190, 93-180, 93-170, 100-205, 100-193, 100-190, 100-180, 100-170, 110-205, 110-193, 110-190, 110-180 or 110-170° C.

In certain embodiments naphtha, light naphtha and/or heavy naphtha refer to such petroleum fractions obtained by crude oil distillation, or distillation of intermediate refinery processes as described herein.

The modifying term "straight run" is used herein having its well-known meaning, that is, describing fractions derived directly from the atmospheric distillation unit, optionally subjected to steam stripping, without other refinery treatment such as hydroprocessing, fluid catalytic cracking or steam cracking. An example of this is "straight run naphtha" and its acronym "SRN" which accordingly refers to "naphtha" defined above that is derived directly from the atmospheric distillation unit, optionally subjected to steam stripping, as is well known.

The term "kerosene" as used herein refers to hydrocarbons boiling in the range of about 170-280, 170-270, 170-260, 180-280, 180-270, 180-260, 190-280, 190-270, 190-260, 193-280, 193-270 or 193-260° C.

The term "light kerosene" as used herein refers to hydrocarbons boiling in the range of about 170-250, 170-235, 170-230, 170-225, 180-250, 180-235, 180-230, 180-225, 190-250, 190-235, 190-230 or 190-225° C.

The term "heavy kerosene" as used herein refers to hydrocarbons boiling in the range of about 225-280, 225-270, 225-260, 230-280, 230-270, 230-260, 235-280, 235-270, 235-260 or 250-280° C.

The term "atmospheric gas oil" and its acronym "AGO" as used herein refer to hydrocarbons boiling in the range of about 250-370, 250-360, 250-340, 250-320, 260-370, 260-360, 260-340, 260-320, 270-370, 270-360, 270-340 or 270-320° C.

The term "heavy atmospheric gas oil" and its acronym "H-AGO" as used herein in certain embodiments refer to the heaviest cut of hydrocarbons in the AGO boiling range including the upper 3-30° C. range (e.g., for AGO having a range of about 250-360° C., the range of H-AGO includes an initial boiling point from about 330-357° C. and an end boiling point of about 360° C.).

The term "medium atmospheric gas oil" and its acronym "M-AGO" as used herein in certain embodiments in conjunction with H-AGO to refer to the remaining AGO after H-AGO is removed, that is, hydrocarbons in the AGO boiling range excluding the upper about 3-30° C. range (e.g., for AGO having a range of about 250-360° C., the range of M-AGO includes an initial boiling point of about 250° C. and an end boiling point of from about 330-357° C.).

In certain embodiments, the term "diesel" is used with reference to a straight run fraction from the atmospheric distillation unit. In embodiments in which this terminology is used, the diesel fraction refers to medium AGO range hydrocarbons and in certain embodiments also in combination with heavy kerosene range hydrocarbons.

The term "atmospheric residue" and its acronym "AR" as used herein refer to the bottom hydrocarbons having an initial boiling point corresponding to the end point of the AGO range hydrocarbons, and having an end point based on the characteristics of the crude oil feed.

The term "vacuum gas oil" and its acronym "VGO" as used herein refer to hydrocarbons boiling in the range of about 370-550, 370-540, 370-530, 370-510, 400-550, 400-540, 400-530, 400-510, 420-550, 420-540, 420-530 or 420-510° C.

The term "light vacuum gas oil" and its acronym "LVGO" as used herein refer to hydrocarbons boiling in the range of about 370-425, 370-415, 370-405, 370-395, 380-425, 390-425 or 400-425° C.

The term "heavy vacuum gas oil" and its acronym "HVGO" as used herein refer to hydrocarbons boiling in the range of about 425-550, 425-540, 425-530, 425-510, 450-550, 450-540, 450-530 or 450-510° C.

The term "vacuum residue" and its acronym "VR" as used herein refer to the bottom hydrocarbons having an initial boiling point corresponding to the end point of the VGO range hydrocarbons, and having an end point based on the characteristics of the crude oil feed.

The term "fuels" refers to crude oil-derived products used as energy carriers. Fuels commonly produced by oil refineries include, but are not limited to, gasoline, jet fuel, diesel fuel, fuel oil and petroleum coke. Unlike petrochemicals, which are a collection of well-defined compounds, fuels typically are complex mixtures of different hydrocarbon compounds.

The terms "kerosene fuel" or "kerosene fuel products" refer to fuel products used as energy carriers, such as jet fuel or other kerosene range fuel products (and precursors for producing such jet fuel or other kerosene range fuel products). Kerosene fuel includes but is not limited to kerosene fuel products meeting Jet A or Jet A-1 jet fuel specifications.

The terms "diesel fuel" and "diesel fuel products" refer to fuel products used as energy carriers suitable for compression-ignition engines (and precursors for producing such fuel products). Diesel fuel includes but is not limited to ultra-low sulfur diesel compliant with Euro V diesel standards.

The term "aromatic hydrocarbons" or "aromatics" is very well known in the art. Accordingly, the term "aromatic hydrocarbon" relates to cyclically conjugated hydrocarbons with a stability (due to delocalization) that is significantly greater than that of a hypothetical localized structure (e.g., Kekule structure). The most common method for determining aromaticity of a given hydrocarbon is the observation of diatropicity in its 1H NMR spectrum, for example the presence of chemical shifts in the range of from 7.2 to 7.3 ppm for benzene ring protons.

The terms "naphthenic hydrocarbons" or "naphthenes" or "cycloalkanes" are used herein having their established meanings and accordingly relates to types of alkanes that have one or more rings of carbon atoms in the chemical structure of their molecules.

The term "wild naphtha" is used herein to refer to naphtha products derived from hydroprocessing units such as distillate hydroprocessing units, diesel hydroprocessing units and/or gas oil hydroprocessing units.

The term "C# hydrocarbons" or "C#", is used herein having its well-known meaning, that is, wherein "#" is an integer value, and means hydrocarbons having that value of carbon atoms. The term "C#+ hydrocarbons" or "C#+" refers to hydrocarbons having that value or more carbon atoms. The term "C#-hydrocarbons" or "C#-" refers to hydrocarbons having that value or less carbon atoms. Similarly, ranges are also set forth, for instance, C1-C3 means a mixture comprising C1, C2 and C3.

The term "petrochemicals" or "petrochemical products" refers to chemical products derived from crude oil that are not used as fuels. Petrochemical products include olefins and aromatics that are used as a basic feedstock for producing chemicals and polymers. Typical olefinic petrochemical products include, but are not limited to, ethylene, propylene, butadiene, butylene-1, isobutylene, isoprene, cyclopentadiene and styrene. Typical aromatic petrochemical products include, but are not limited to, benzene, toluene, xylene, and ethyl benzene.

The term "olefin" is used herein having its well-known meaning, that is, unsaturated hydrocarbons containing at least one carbon-carbon double bond. In plural, the term "olefins" means a mixture comprising two or more unsaturated hydrocarbons containing at least one carbon-carbon double bond. In certain embodiments, the term "olefins" relates to a mixture comprising two or more of ethylene, propylene, butadiene, butylene-1, isobutylene, isoprene and cyclopentadiene.

The term "BTX" as used herein refers to the well-known acronym for benzene, toluene and xylenes.

The term "make-up hydrogen" is used herein with reference to hydroprocessing zones to refer to hydrogen requirements of the zone that exceed recycle from conventionally integrated separation vessels; in certain embodiments as used herein all or a portion of the make-up hydrogen in any given hydroprocessing zone or reactor within a zone is from gases derived from the steam cracking zone(s) in the integrated processes and systems.

The term "crude to chemicals conversion" as used herein refers to conversion of crude oil into petrochemicals including but not limited to lower olefins such as ethylene, propylene, butylenes (including isobutylene), butadiene, MTBE, butanols, benzene, ethylbenzene, toluene, xylenes, and derivatives of the foregoing.

The term "crude to chemicals conversion ratio" as used herein refers to the ratio, on a mass basis, of the influent crude oil before desalting, to petrochemicals.

The term "crude C4" refers to the mixed C4 effluent from a steam cracking zone.

The term "C4 Raffinate 1" or "C4 Raff-1" refers to the mixed C4s stream leaving the butadiene extraction unit, that is, mixed C4s from the crude C4 except butadiene.

The term "C4 Raffinate 2" or "C4 Raff-2" refers to the mixed C4s stream leaving the MTBE unit, that is, mixed C4s from the crude C4 except butadiene and isobutene.

The term "C4 Raffinate 3" or "C4 Raff-3" refers to the mixed C4s stream leaving the C4 distillation unit, that is, mixed C4s from the crude C4 except butadiene, isobutene, and butane-1.

The terms "pyrolysis gasoline" and its abbreviated form "py-gas" are used herein having their well-known meaning, that is, thermal cracking products in the range of C5 to C9, for instance having an end boiling point of about 204.4° C. (400° F.), in certain embodiments up to about 148.9° C. (300° F.).

The terms "pyrolysis oil" and its abbreviated form "py-oil" are used herein having their well-known meaning, that is, a heavy oil fraction, C10+, that is derived from steam cracking.

The terms "light pyrolysis oil" and its acronym "LPO" as used herein in certain embodiments refer to pyrolysis oil having an end boiling point of about 440, 450, 460 or 470° C.

The terms "heavy pyrolysis oil" and its acronym "HPO" as used herein in certain embodiments refer to pyrolysis oil having an initial boiling point of about 440, 450, 460 or 470° C.

In general, the integrated process for producing petrochemicals and fuel products from a crude oil feed includes an initial separation step to separate from a crude oil feed in an atmospheric distillation zone at least a first atmospheric distillation zone fraction comprising straight run naphtha; a second atmospheric distillation zone fraction comprising at least a portion of middle distillates, and a third atmospheric distillation zone fraction comprising atmospheric residue. A first vacuum distillation zone fraction comprising vacuum gas oil is separated from the third atmospheric distillation zone fraction in a vacuum distillation zone. In a distillate hydroprocessing ("DHP") zone, such as a diesel hydrotreater, at least a portion of the second atmospheric distillation zone fraction is processed to produce at least a first DHP fraction and a second DHP fraction, wherein the first DHP fraction comprises naphtha and the second DHP fraction is used for diesel fuel production. The first vacuum distillation zone fraction (and optionally all or a portion of an atmospheric gas oil fraction, or all or a portion of a heavy atmospheric gas oil fraction) is processed in a gas oil hydrotreating zone to produce naphtha, middle distillates, and hydrotreated gas oil. Hydrotreated gas oil is processed in a gas oil steam cracking zone.

At least the first atmospheric distillation zone fraction and a pyrolysis gasoline raffinate from an aromatics extraction zone are processed in a mixed feed steam cracking zone. The products from the mixed feed steam cracking zone and the gas oil steam cracking zone include integrated or separate mixed product stream(s) comprising $H_2$, methane, ethane, ethylene, mixed C3s and mixed C4s; pyrolysis gasoline stream(s); and pyrolysis oil stream(s).

From the mixed product stream(s) C3s and the mixed C4s, petrochemicals ethylene, propylene and butylenes are recovered. Ethane and non-olefinic C3s are recycled to the mixed feed steam cracking zone, and non-olefinic C4s are recycled to the mixed feed steam cracking zone or to a separate processing zone for production of additional petrochemicals. Pyrolysis gasoline is treated in a py-gas hydroprocessing zone to produce hydrotreated pyrolysis gasoline. The hydrotreated pyrolysis gasoline is routed to the aromatics extraction zone to recover aromatic products and the aromatics extraction zone raffinate that is recycled to the mixed feed steam cracking zone.

Ethane and non-olefinic C3s and C4s are recovered, with ethane and non-olefinic C3s recycled to the steam cracking complex, and non-olefinic C4s recycled to the steam cracking complex or passed to a separate processing zone for production of additional petrochemicals such as propylene and/or mixed butanol liquids. Pyrolysis gasoline is treated in a py-gas hydroprocessing zone to produce hydrotreated pyrolysis gasoline, which is routed to an aromatics extraction complex to recover aromatic petrochemicals and a raffinate, including pyrolysis gasoline raffinate that is recycled to the steam cracking complex.

Figure 2:
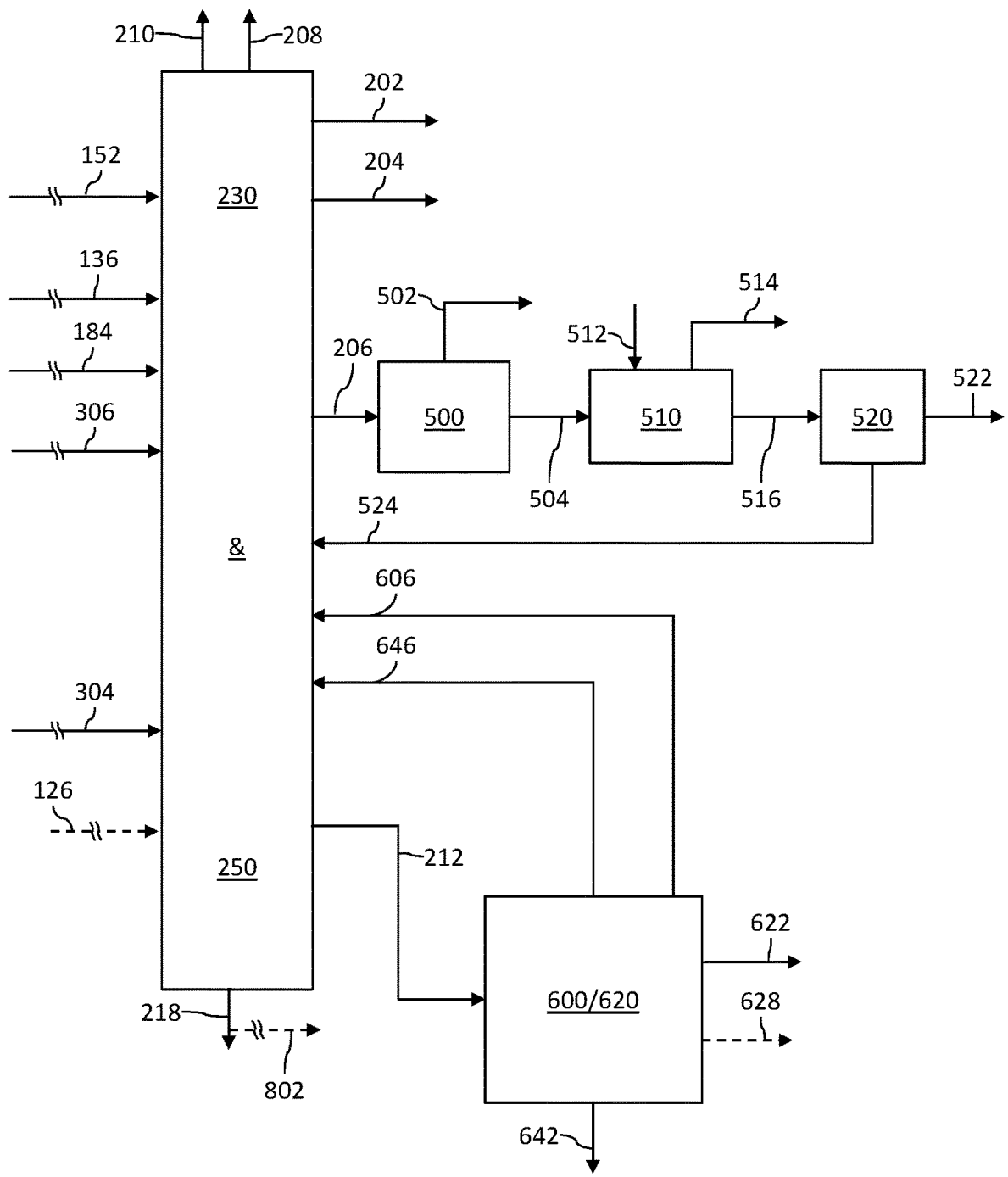
FIG. 2 schematically depicts operations downstream of and including a steam cracker complex in embodiments of processes for producing petrochemicals and fuel product.

FIGS. 1 and 2 schematically depict embodiments of processes and systems for conversion of crude oil to petrochemicals and fuel products, including a mixed feed steam cracking zone and a gas oil steam cracking zone. Generally, FIG. 1 shows operations upstream of a mixed feed steam cracking zone ("MFSC") 230 and a gas oil steam cracking zone 250 while FIG. 2 shows operations downstream of the crude oil conversion zone and including the mixed feed steam cracking zone 230 and the gas oil steam cracking zone 250. The mixed feed steam cracking zone and the gas oil steam cracking zone are shown for simplicity in a single schematic block 230/250 in FIGS. 2, 3, 4 and 5.

In the description herein, both the mixed feed steam cracking zone 230 and the gas oil steam cracking zone 250 are collectively referred to as the "steam cracker complex" 230/250 in certain instances, although a person having ordinary skill in the art will appreciate that the different steam cracking zones contain different furnaces and associated exchangers, with certain products from each combined for further downstream operations. In certain embodiments quench systems and fractionation units can be combined. In additional embodiments separate quench systems and fractionation units can be used for each of the mixed feed steam cracking zone 230 and the gas oil steam cracking zone 250.

With reference to FIG. 1, a crude oil feed 102, in certain embodiments AXL or AL, is separated into fractions in a crude complex 100, typically including an atmospheric distillation zone ("ADU") 110, a saturated gas plant 150 and a vacuum distillation zone ("VDU") 160. The crude oil feed 102, in certain embodiments having LPG and light naphtha removed, is separated into fractions in the atmospheric distillation zone 110. As shown in FIG. 1, light products, for instance, light hydrocarbons with fewer than six carbons, are passed to the mixed feed steam cracking zone 230. In particular, C2-C4 hydrocarbons 152 including ethane, propane and butanes are separated from the light ends and LPG 112 from the atmospheric distillation zone 110 via the saturated gas plant 150. Optionally, other light products are routed to the saturated gas plant 150, shown in dashed lines as stream 156, such as light gases from refinery units within the integrated system, and in certain embodiments light gases from outside of the battery limits. The separated C2-C4 hydrocarbons 152 are routed to the mixed feed steam cracking zone 230. Off-gases 154 from the saturated gas plant 150 and off-gases 208 from the mixed feed steam cracking zone 230 and gas oil steam cracking zone 250 are removed and recovered as is typically known, for instance to contribute to a fuel gas ("FG") system.

Straight run naphtha 136 from the atmospheric distillation zone 110 is passed to the mixed feed steam cracking zone 230. In certain embodiments, all, a substantial portion or a significant portion of the straight run naphtha 136 is routed to the mixed feed steam cracking zone 230. Remaining naphtha (if any) can be added to a gasoline pool. In addition, in certain embodiments the straight run naphtha stream 136 contains naphtha from other sources as described herein and sometimes referred to as wild naphtha, for instance, naphtha range hydrocarbons from one or more of the integrated distillate, gas oil and/or residue hydroprocessing units.

Middle distillates are used to produce diesel and/or kerosene, and additional feed to the mixed feed steam cracking zone 230. In the embodiments shown in FIG. 1, at least three different middle distillate cuts are processed for production of fuel products and petrochemicals (via the steam cracker). In one example using the arrangement shown in FIG. 1, a first atmospheric distillation zone middle distillate fraction 116, in certain embodiments referred to as a kerosene fraction, contains light kerosene range hydrocarbons, a second atmospheric distillation zone middle distillate fraction 122, in certain embodiments referred to as a diesel fraction, contains heavy kerosene range hydrocarbons and medium AGO range hydrocarbons, and a third atmospheric distillation zone middle distillate fraction 126, in certain embodiments referred to as an atmospheric gas oil fraction, contains heavy AGO range hydrocarbons. In another example using the arrangement shown in FIG. 1, a first middle distillate fraction 116 contains kerosene range hydrocarbons, a second middle distillate fraction 122 contains medium AGO range hydrocarbons and a third middle distillate fraction 126 contains heavy AGO range hydrocarbons. In another example using the arrangement shown in FIG. 1, a first middle distillate fraction 116 contains light kerosene range hydrocarbons and a portion of heavy kerosene range hydrocarbons, a second middle distillate fraction 122 contains a portion of heavy kerosene range hydrocarbons and a portion of medium AGO range hydrocarbons and a third middle distillate fraction 126 contains a portion of medium AGO range hydrocarbons and heavy AGO range hydrocarbons.

For example, a first middle distillate fraction 116 can be processed in a kerosene sweetening process 170 to produce kerosene fuel product 172, for instance, jet fuel compliant with Jet A or Jet A-1 specifications, and optionally other fuel products (not shown). In certain embodiments herein, all or a portion of the first middle distillate fraction 116 is not used for fuel production, but rather is used as a feed for distillate hydroprocessing so as to produce additional feed for the mixed feed steam cracking zone 230.

A second middle distillate fraction 122 is processed in a distillate hydroprocessing zone such as a diesel hydrotreating zone 180, to produce wild naphtha 184 and a diesel fuel fraction 182, for instance, compliant with Euro V diesel standards. In additional embodiments, all or a portion of the first middle distillate fraction 116 can be treated with the second middle distillate fraction 122, as denoted by dashed lines.

All or a portion of the wild naphtha 184 is routed to the mixed feed steam cracking zone 230; any portion that is not passed to the mixed feed steam cracking zone 230 can be routed to the gasoline pool. In certain embodiments, the wild naphtha 184 is routed through the crude complex 100, alone, or in combination with other wild naphtha fractions from within the integrated process. In embodiments in which the wild naphtha 184 is routed through the crude complex 100, all or a portion of the liquefied petroleum gas produced in the diesel hydrotreating zone 180 can be passed with the wild naphtha. In certain embodiments, all, a substantial portion, a significant portion or a major portion of the wild naphtha 184 is routed to the mixed feed steam cracking zone 230 (directly or through the crude complex 100).

In certain embodiments (as denoted by dashed lines), all, a substantial portion, a significant portion or a major portion of the third middle distillate fraction 126 is routed to the vacuum gas oil hydroprocessing zone in combination with the vacuum gas oil stream 162; any portion that is not passed to the vacuum gas oil hydroprocessing zone can be routed to the gas oil steam cracking zone 250 without hydroprocessing. In further embodiments (as denoted by dashed lines), all, a substantial portion, a significant portion or a major portion of the third middle distillate fraction 126 is routed to the gas oil steam cracking zone 250 without hydroprocessing, and any portion that is not passed to the gas oil steam cracking zone 250 is routed to the vacuum gas oil hydroprocessing zone.

An atmospheric residue fraction 114 from the atmospheric distillation zone 110 is further separated in the vacuum distillation zone 160. Vacuum gas oil 162 from the vacuum distillation zone 160 is routed to the vacuum gas oil hydrotreating zone 300. In certain embodiments, vacuum gas oil 162 can bypass the vacuum gas oil hydrotreating zone 300 and be routed to the gas oil steam cracking zone 250 (not shown). The heaviest fraction 168 from the vacuum distillation zone 160, vacuum residue, can be sent to a fuel oil ("FO") pool and/or optionally processed in a residue treatment zone 800, shown in dashed lines. In certain embodiments, a minor portion of the atmospheric residue fraction 114 can bypass the vacuum distillation zone 160 (not shown) and is routed to the optional residue treating zone 800 and/or the gas oil steam cracking zone 250 (not shown).

The vacuum gas oil hydrotreating zone 300 can operate under mild, moderate or severe hydrotreating conditions, and generally produces some light produces, which can be routed to the diesel hydrotreating zone 180 (not shown in FIG. 1 and/or can be recovered as a wild naphtha fraction 306, and hydrotreated gas oil 304. In certain embodiments, all, a substantial portion, a significant portion or a major portion of the total vacuum gas oil 162 is routed to the vacuum gas oil hydrotreating zone 300. The remainder (if any) can be routed directly to the gas oil steam cracking zone 250, bypassing the vacuum gas oil hydrotreating zone. In addition to vacuum gas oil and optionally atmospheric gas oil, in certain embodiments the vacuum gas oil hydrotreating zone 300 can also process atmospheric and/or vacuum gas oil range products from an optional vacuum residue treatment zone 800. A hydrotreated gas oil fraction 304 from the gas oil hydrotreating zone 300 generally contains the portion of the gas oil hydrotreating zone 300 effluent that is at or above the AGO, H-AGO or VGO boiling range.

All, a substantial portion, a significant portion or a major portion of the naphtha fraction 306 from the gas oil hydrotreating zone 300 is routed to the mixed feed steam cracking zone 230. Remaining wild naphtha (if any) can be added to a gasoline pool. In certain embodiments, the naphtha fraction 306 is routed through the crude complex 100. In embodiments in which the hydrotreated naphtha fraction 306 is routed through the crude complex 100, all or a portion of the liquefied petroleum gas produced in the gas oil hydrotreating zone 300 can be passed with the hydrotreated naphtha fraction 306.

All, a substantial portion or a significant portion of the hydrotreated gas oil fraction 304 from the gas oil hydrotreating zone 300 is routed to the gas oil steam cracking zone 250. The remainder (if any) can be recycled and further hydroprocessed and/or bled from the system and/or passed to the optional vacuum residue treating zone.

In certain embodiments, at least a major portion of a vacuum residue fraction 168 from the vacuum distillation zone 160 is passed to the optional vacuum residue treatment zone 800. In certain embodiments, all, a substantial portion, a significant portion or a major portion of the total vacuum residue 168 is routed to the optional vacuum residue treatment zone 800. The remainder (if any) is routed to the fuel oil pool (not shown). In addition, in certain embodiments, a minor portion of the atmospheric residue fraction 114 can bypass the vacuum distillation zone 160 (not shown) and be routed to the optional vacuum residue treatment zone 800. In certain embodiments, all or a portion of a pyrolysis oil stream 218 from the steam cracker complex, for instance, shown as stream 902, can be processed in the optional vacuum residue treatment zone 800.

With reference to FIG. 2, the mixed feed steam cracking zone 230 and the gas oil steam cracking zone 250 operate to convert their respective feeds into ethylene 202, propylene 204, mixed C4s 206, pyrolysis gasoline 212, pyrolysis oil 218, and off-gases 208 that can be passed to an integrated fuel gas system. Further, hydrogen 210 is recovered from the cracked products and can be recycled to hydrogen users within the complex limits. Not shown are the ethane and propane recycle, which are typical in steam cracking operations, although it is appreciated that in certain embodiments all or a portion of the ethane and propane can be diverted. In certain embodiments, all, a substantial portion, a significant portion or a major portion of ethane is recycled to the mixed feed steam cracking zone 230, and all, a substantial portion, a significant portion or a major portion of propane is mixed feed steam cracking zone 230. In certain embodiments hydrogen for all hydrogen users in the integrated process and system is derived from hydrogen 210 recovered from the cracked products, and no outside hydrogen is required once the process has completed start-up and reached equilibrium. In further embodiments excess hydrogen can be recovered.

For simplicity, operations in an olefins recovery train are not shown, but are well known and are considered part of the mixed feed steam cracking zone 230 and gas oil steam cracking zone 250 as described herein with respect to FIGS. 2, 3, 4 and 5.

The mixed C4s stream 206 containing a mixture of C4s from the steam cracker complex 230/250, known as crude C4s, is routed to a butadiene extraction unit 500 to recover a high purity 1,3-butadiene product 502. A first raffinate 504 ("C4-Raff-1") containing butanes and butenes is passed to a selective hydrogenation unit ("SHU") and methyl tertiary butyl ether ("MTBE") unit, SHU and MTBE zone 510, where it is mixed with high purity fresh methanol 512 from outside battery limits to produce methyl tertiary butyl ether 514.

A second raffinate 516 ("C4 Raff-2") from the SHU and MTBE zone 510 is routed to a C4 distillation unit 520 for separation into a 1-butene product stream 522 and an alkane stream 524 (a third raffinate "C4 Raff-3") containing residual C4s, all, a substantial portion, a significant portion or a major portion of which is recycled to the mixed feed steam cracking zone 230 although it is appreciated that in certain embodiments all or a portion of the residual C4s can be diverted. Separation of the ethylene 202, propylene 204 and the mixed C4s stream 206 occurs in a suitable arrangement of known separation steps for separating steam cracking zone effluents, including compression stage(s), depropanizer, debutanizer, demethanizer and deethanizer.

All, a substantial portion or a significant portion of the pyrolysis gasoline 212 from the steam cracker complex 230/250 is fed to a py-gas hydrotreatment and recovery center 600/620. In certain embodiments, select hydrocarbons having 5-12 carbons are recovered from untreated pyrolysis gasoline and the remainder is subsequently hydrotreated for aromatics recovery. In a py-gas hydrotreating unit, diolefins and olefins in the pyrolysis gasoline are saturated.

Hydrotreated pyrolysis gasoline from the py-gas hydrotreating unit (in certain embodiments having C5s removed and recycled to the mixed feed steam cracking zone 230 instead of or in conjunction with C5s from the aromatics extraction zone 620) is routed to the aromatics extraction zone 620. The py-gas hydrotreating zone 600 and the aromatics extraction zone 620 are shown for simplicity in a single schematic block 600/620 in FIGS. 2, 3, 4 and 5.

The aromatics extraction zone 620 includes, for instance, one or more extractive distillation units, and operates to separate the hydrotreated pyrolysis gasoline into an aromatics stream 622 containing high-purity benzene, toluene, xylenes and C9 aromatics, which are recovered for chemical markets. C5 raffinate 606 and non-aromatics 646 (for instance, C6-C9) are recycled to the mixed feed steam cracking zone 230. In certain embodiments, all, a substantial portion or a significant portion of the C5 raffinate 606 and non-aromatics 646 are passed to the mixed feed steam cracking zone 230. A heavy aromatics stream 642 (for instance, C10-C12) can be used as an aromatic solvent, an octane boosting additive or as a cutter stock into a fuel oil pool. In certain embodiments ethylbenzene 628 can be recovered.

In certain embodiments, pyrolysis oil 218 can be blended into the fuel oil pool. In additional embodiments, pyrolysis oil 218 can be fractioned (not shown) into light pyrolysis oil and heavy pyrolysis oil. For instance, light pyrolysis oil can be blended with the first middle distillate stream 116 and/or the second middle distillate stream 122, for processing to produce diesel fuel product and/or additional feed to the mixed feed steam cracking zone 230. In further embodiments light pyrolysis oil derived from pyrolysis oil 218 can be processed in the vacuum gas oil hydrotreating zone 300. In additional embodiments, light pyrolysis oil derived from pyrolysis oil 218 can be blended into the fuel oil pool. In further embodiments, light pyrolysis derived from pyrolysis oil 218 can be processed in the residue treating zone 800. In certain embodiments, all, a substantial portion, a significant portion or a major portion of light pyrolysis oil derived from pyrolysis oil 218 can be passed to one or both of the diesel hydrotreating zone 180 and/or the vacuum gas oil hydrotreating zone 300; any remainder can be blended into the fuel oil pool. Heavy pyrolysis oil can be blended into the fuel oil pool, used as a carbon black feedstock and/or processed in the optional residue treating zone 800. In certain embodiments, all, a substantial portion, a significant portion or a major portion of the pyrolysis oil 218 (light and heavy) can be processed in the optional residue treating zone 800.

Figure 3:
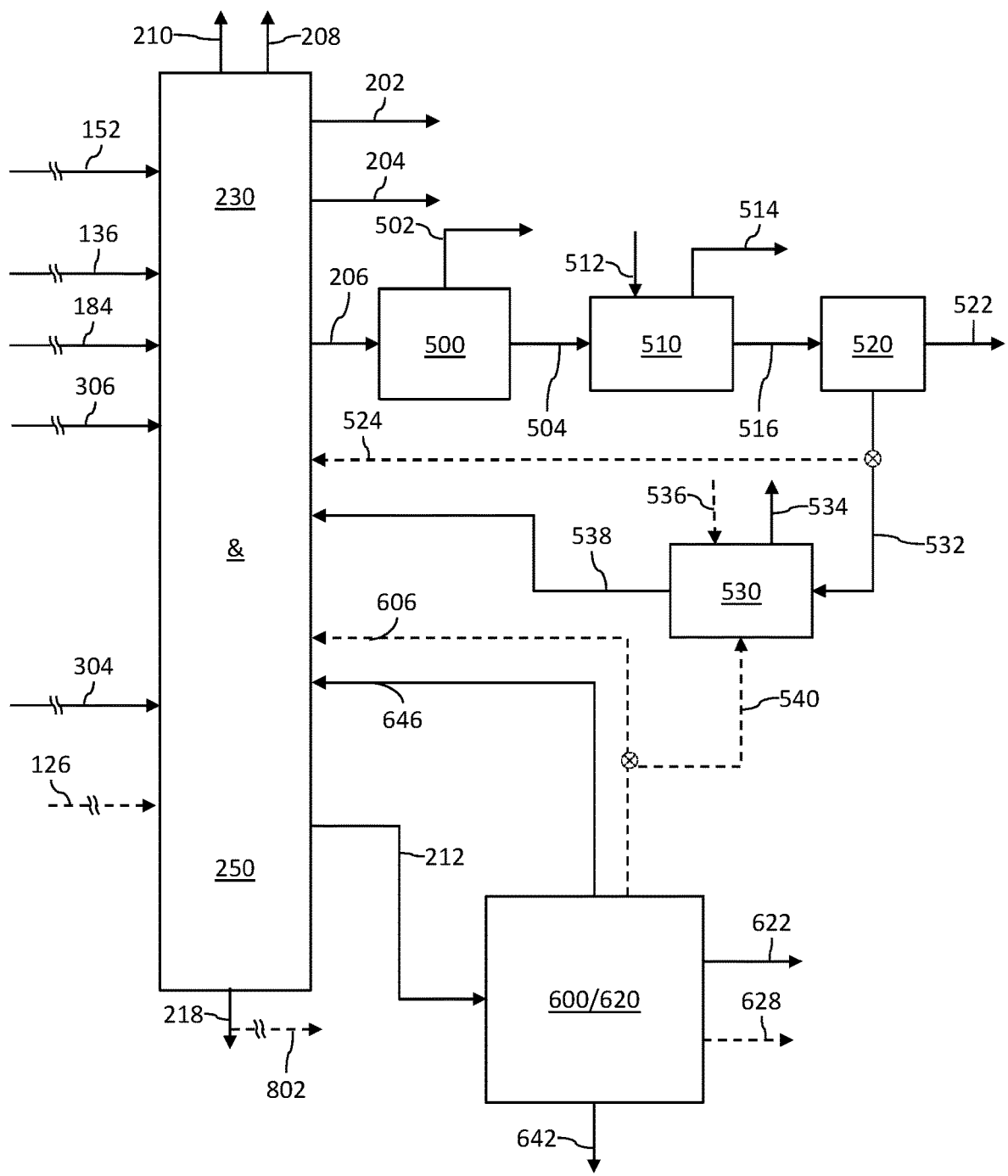
FIG. 3 schematically depicts operations downstream of and including a steam cracker complex in embodiments of processes for producing petrochemicals integrating metathesis.

FIG. 3 schematically depicts further embodiments of processes and systems for conversion of crude oil to petrochemicals and fuel products, with metathesis conversion of C4 and C5 olefins to produce additional propylene. The process operates as described with respect to FIG. 1 upstream of the steam cracking operations.

Downstream of the steam cracking operations, the butadiene extraction train can optionally operate in a manner similar to that in FIG. 2 shown as the third C4 raffinate stream 524 from a diverter (in dashed lines) from the C4 distillation unit 520 directly to the mixed feed steam cracking zone 230.

In a metathesis mode of operation, a mixed C4 raffinate stream 532 ("C4 Raff 3") from the C4 distillation unit 520 and C5 raffinate 540 from the py-gas hydrotreatment and recovery center 600/620 are routed to a metathesis unit 530 for metathesis conversion to additional propylene 534. In certain embodiments, all, a substantial portion, a significant portion or a major portion of the cracked C5s from the py-gas hydrotreater can be routed to the metathesis unit 530 prior to aromatics extraction. As indicated, a portion 536 of the ethylene product 202 can be routed to the metathesis unit 530. In additional embodiments, ethylene for the metathesis unit 530 is supplied from outside the complex limits, instead of or in addition to the portion 536 of the ethylene product 202.

Selective recovery of various alkene and diene pyrolysis chemicals having four carbons, and metathesis conversion to produce additional propylene, is achieved using a metathesis unit 530. A stream 538 containing a mixture of mostly saturated C4/C5 from the metathesis unit 530 is recycled to the mixed feed steam cracking unit 230.

As in FIG. 2, in the configuration of FIG. 3, pyrolysis gasoline 212 from the steam cracker complex 230/250 is routed to the py-gas hydrotreatment and recovery center 600/620; C6-C9 aromatics stream 622, BTX, is recovered for chemical markets; C6-C9 non-aromatics stream 646 is recycled to the mixed feed steam cracking zone 230; and the heavy aromatics stream 642 (for instance, C10-C12 products) is recovered. In certain embodiments ethylbenzene 628 can be recovered. In addition, in a metathesis mode of operation, a C5 raffinate is routed to the metathesis unit 530, shown as stream 540. Optionally C5 raffinate is recycled to the mixed feed steam cracking zone 230 (as in the embodiments of FIG. 2) via stream 606, shown in dashed lines in FIG. 3. In certain embodiments (not shown), all or a portion of the cracked C5s from the py-gas hydrotreater can be routed to the metathesis unit 530 prior to aromatics extraction.

In the configuration depicted in FIG. 3, an optional diverter is shown, indicated as a diverter and stream in dashed lines, to bypass the metathesis conversion process, to therefore divert all, a substantial portion, a significant portion or a major portion of the third C4 raffinate stream 524 to the mixed feed steam cracking zone 230. In a metathesis mode, flow can be directed to the metathesis conversion unit 530. In further alternative modes, flow of the third C4 raffinate stream 524 can be directed to the mixed feed steam cracking zone 230 and the metathesis conversion unit 530. In this manner, a producer can vary the quantity of feed to tailor the desired outputs. Accordingly, 0-100% of the third C4 raffinate stream 524 can be routed to the metathesis conversion unit 530, and the remainder (if any) is directed to the mixed feed steam cracking zone 230. The quantity can be determined, for instance, based upon demand for ethylene, demand for propylene, and/or minimum ranges for which the unit is operated depending on design capacity.

Figure 4:
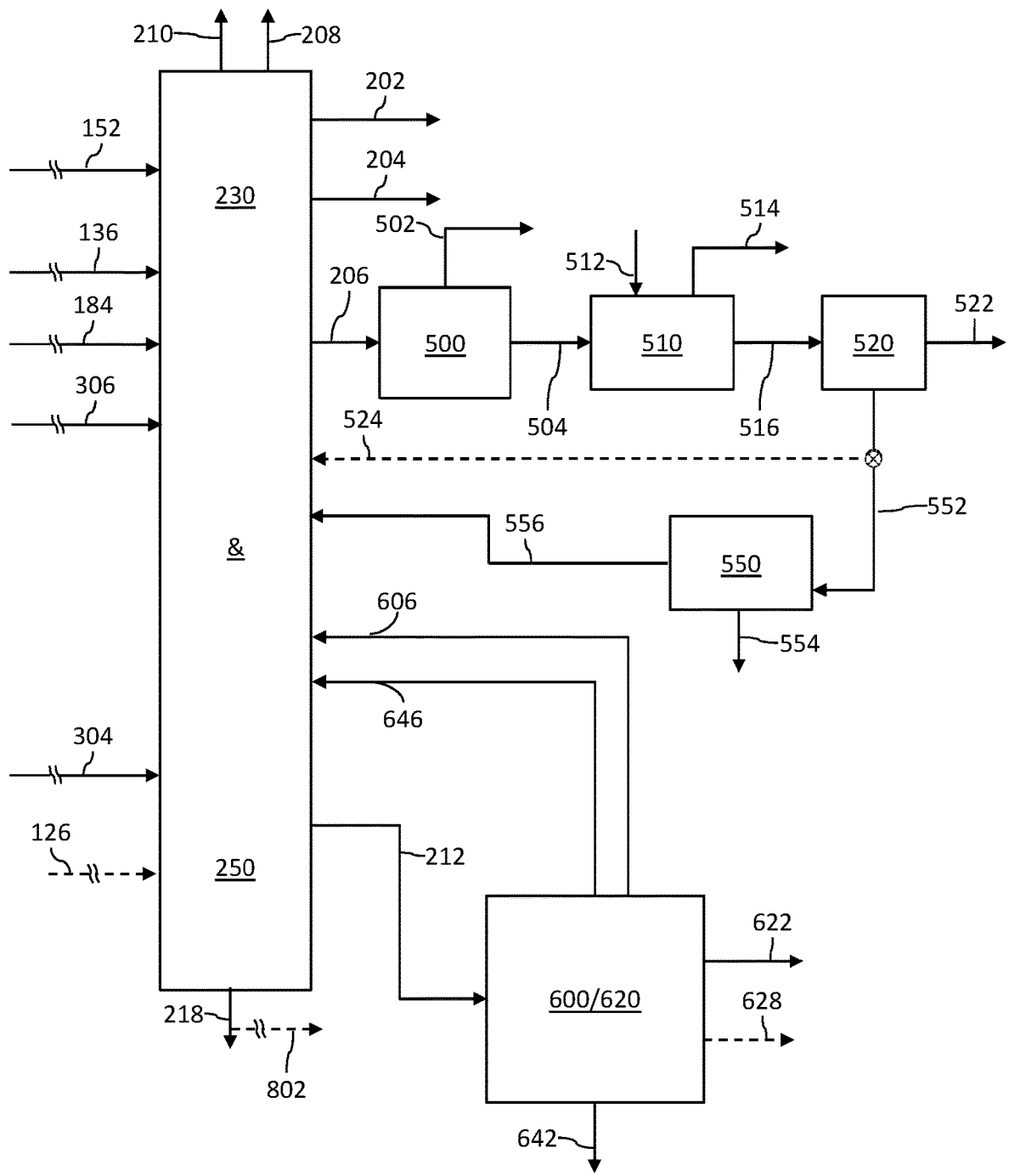
FIG. 4 schematically depicts operations downstream of and including a steam cracker complex in embodiments of processes for producing petrochemicals and fuel products integrating mixed butanol production.

FIG. 4 schematically depicts further embodiments of processes and systems for conversion of crude oil to petrochemicals and fuel products. The process operates as described with respect to FIG. 1 upstream of the steam cracking operations. In this embodiment, an additional step is provided to convert a mixture of butenes into mixed butanols suitable as a gasoline blending oxygenate and for octane enhancement. Suitable processes to convert a mixture of butenes into mixed butanols are described in one or more of commonly owned patent publications US20160115107A1, US20150225320A1, US20150148572A1, US20130104449A1, US20120245397A1 and commonly owned U.S. Pat. No. 9,447,346B2, U.S. Pat. No. 9,393,540B2, U.S. Pat. No. 9,187,388B2, U.S. Pat. No. 8,558,036B2, all of which are incorporated by reference herein in their entireties. In certain embodiments, a particularly effective conversion process known as "SuperButol™" technology is integrated, which is a one-step process that converts a mixture of butenes into mixed butanol liquids.

Downstream of the steam cracking operations, the butadiene extraction train can optionally operate in a manner similar to that in FIG. 2 shown as the stream 524 from a diverter (in dashed lines) from the C4 distillation unit 520 directly to the mixed feed steam cracking zone 230. A mixed butanols production zone 550 is integrated for selective recovery of various alkene and diene pyrolysis chemicals having four carbons, and in certain processing arrangements hydrating a portion of those C4's in a butanol production unit (such as a "SuperButol™" unit) to produce high value fuel additives.

For instance, the mixed butanols production zone 550 operates to convert butenes to butanols from undervalued refinery/petrochemical mixed olefin streams. The butanols provide an alternative option for oxygenates in gasoline blends. The crude C4 processing center 550 includes the conversion reaction of butenes to butanols, for instance, in one or more high pressure catalytic reactors followed by gravity separation of butenes and butanols from water, and subsequent separation of the butanols product from butenes by distillation. Process stages include butenes and water make-up and recycle, butanol reaction, high pressure separation, low pressure separation, debutenizer distillation (product column) and an aqueous distillation column.

FIG. 4 depicts embodiments in which a C4 raffinate stream 552 containing butenes from the C4 distillation unit 520 routed to the mixed butanols production zone 550 to convert the mixture of butenes into mixed butanol liquids 554. In certain embodiments, all, a substantial portion, a significant portion or a major portion of stream 552 is routed to the butanol production unit 550. Alkanes 556 are recycled to the mixed feed steam cracking zone 230.

As in FIGS. 1 and 2 in the configuration of FIG. 4, pyrolysis gasoline 212 from the steam cracker complex 230/250 is routed to the py-gas hydrotreatment and recovery center 600/620; C6-C9 aromatics stream 622 are recovered for chemical markets, C5 raffinate 606 and non-aromatics 646 (for instance, C6-C9) are recycled to the mixed feed steam cracking zone 230, and the heavy aromatics stream 642 (for instance, C10-C12 products) is recovered. In certain embodiments ethylbenzene 628 can be recovered.

In the configuration depicted in FIG. 4, an optional diverter is shown, indicated as a diverter and stream in dashed lines, to bypass the process for conversion of a mixture of butenes into mixed butanols, to therefore divert all, a substantial portion, a significant portion or a major portion of the C4 Raff-3 524 to the mixed feed steam cracking zone 230. In a mixed butanol liquid mode of operation, flow can be directed to the mixed butanols production zone 550 for conversion of a mixture of butenes into mixed butanols. In further alternative modes, flow of the C4 Raff-3 524 can be directed to the mixed feed steam cracking zone 230 and the mixed butanols production zone 550. In this manner, a producer can vary the quantity of feed to tailor the desired outputs. Accordingly, 0-100% of the third C4 raffinate stream 524 can be routed to mixed butanols production zone 550, and the remainder (if any) is directed to the mixed feed steam cracking zone 230. The quantity can be determined, for instance, based upon demand for ethylene, demand for mixed butanols, and/or minimum ranges for which the unit is operated depending on design capacity.

Figure 5:
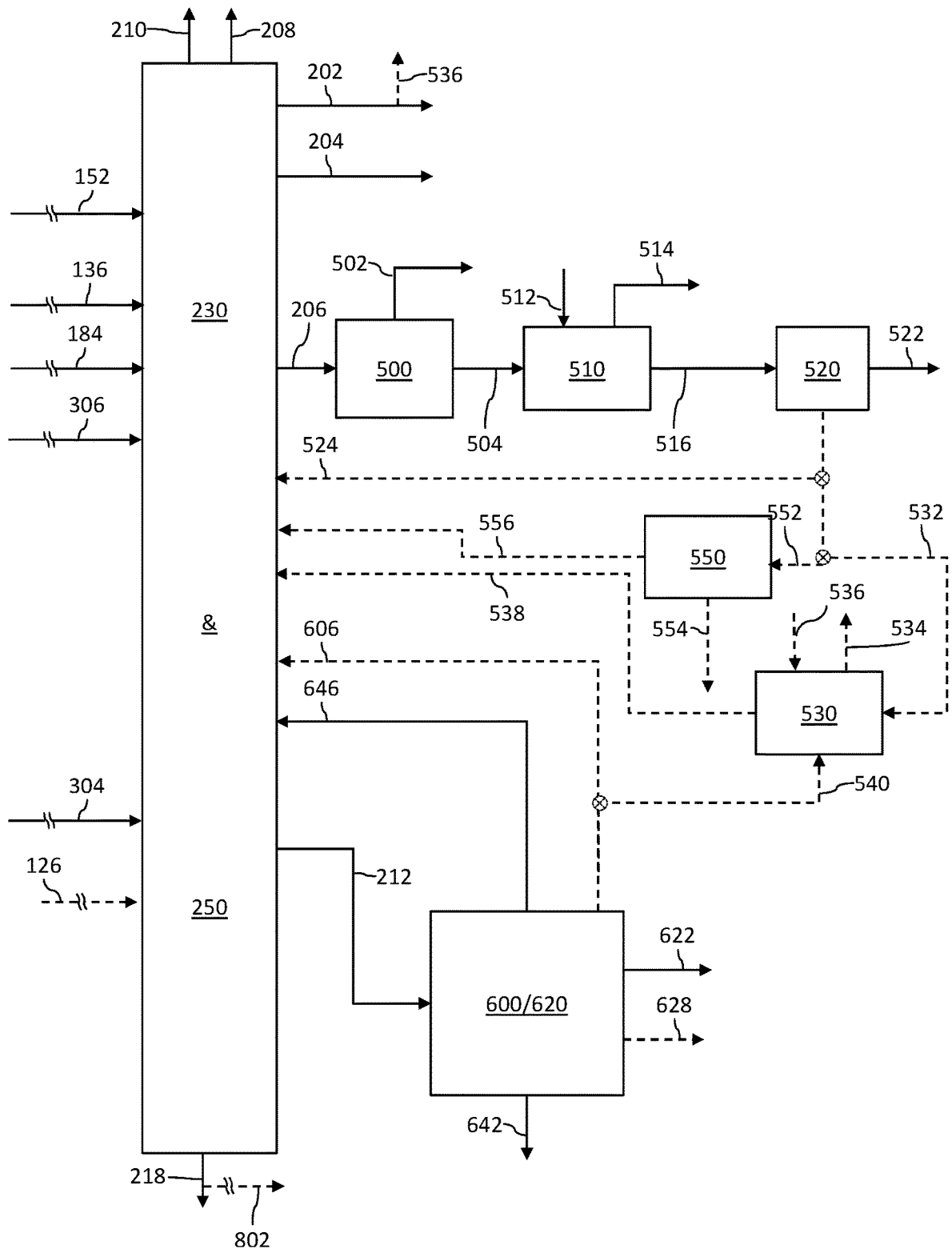
FIG. 5 schematically depicts operations downstream of and including a steam cracker complex in embodiments of processes for producing petrochemicals and fuel products integrating metathesis and mixed butanol production.

FIG. 5 schematically depicts further embodiments of processes and systems for conversion of crude oil to petrochemicals and fuel products. In this embodiment, additional step(s) of metathesis conversion of C4 and C5 olefins to produce additional propylene, and/or conversion of a mixture of butenes into mixed butanols suitable as a gasoline blending oxygenate and for octane enhancement, are integrated. The process operates as described with respect to FIG. 1 upstream of the steam cracking operations.

Downstream of the steam cracking operations, the butadiene extraction train can optionally operate in a manner similar to that in FIG. 2 shown as the stream 524 from a diverter (in dashed lines) from the C4 distillation unit 520 directly to the mixed feed steam cracking zone 230 as an optional mode of operation. The configuration in FIG. 5 integrates selective recovery of various alkene and diene pyrolysis chemicals having four carbons, metathesis conversion to produce additional propylene, and/or conversion of a mixture of butenes into mixed butanols suitable as a gasoline blending oxygenate and for octane enhancement.

FIG. 5 depicts a stream 552 containing butenes from the C4 distillation step ("C4 Raff-3") that can be routed to a mixed butanols production zone 550 for conversion of the mixture of butenes into mixed butanol liquids 554. Alkanes 556 are recycled to the mixed feed steam cracking zone 230. In addition, a portion 532 of the 2-butene rich raffinate-3 from the C4 distillation unit 520 is passed to a metathesis unit 530 for metathesis conversion to additional propylene 534. As indicated, a portion 536 of the ethylene product 202 can be routed to the metathesis unit 530. A stream 538, having a mixture of mostly saturated C4/C5 from metathesis unit, is recycled to the mixed feed steam cracking zone 230.

As in FIG. 2, in the configuration of FIG. 5, pyrolysis gasoline 212 from the steam cracker complex 230/250 is routed to the py-gas hydrotreatment and recovery center 600/620; C6-C9 aromatics stream 622, BTX, is recovered for chemical markets; non-aromatics 646 (for instance, C6-C9) is recycled to the mixed feed steam cracking zone 230, and the heavy aromatics stream 642 (for instance, C10-C12 products) is recovered. In certain embodiments ethylbenzene 628 can be recovered. The raffinate stream 540 can be routed to the metathesis unit 530, as shown, and/or optionally recycled to the mixed feed steam cracking zone 230 as shown in dashed lines, stream 606. In certain embodiments (not shown), all or a portion of the cracked C5s from the py-gas hydrotreater can be routed to the metathesis unit 530 prior to aromatics extraction.

In the configuration depicted in FIG. 5, an optional diverter is shown, indicated as a diverter and stream in dashed lines, to bypass the metathesis conversion process and the process for conversion of a mixture of butenes into mixed butanols, to therefore divert all, a substantial portion, a significant portion or a major portion of the C4 Raff-3 524 to the mixed feed steam cracking zone 230. An optional valve also can be provided to direct flow of the C4 Raff-3 to one or both of the metathesis conversion unit 530 and/or the mixed butanols production zone 550 for conversion of a mixture of butenes into mixed butanols. In further alternative modes, flow of the C4 Raff-3 524 can be directed to each of the mixed feed steam cracking zone 230, the metathesis conversion unit 530 (as stream 532), and the mixed butanols production zone 550 (as stream 552). In this manner, a producer can vary the quantity of feed to tailor the desired outputs. Accordingly, all, a substantial portion, a significant portion or a major portion of the third C4 raffinate stream can be routed to the metathesis conversion unit 530, and the remainder (if any) is directed to the mixed feed steam cracking zone 230 and/or the mixed butanols production zone 550. In certain embodiments, all, a substantial portion, a significant portion or a major portion of the third C4 raffinate stream is routed to the metathesis conversion unit 530, and the remainder (if any) is directed to the mixed feed steam cracking zone 230. In further embodiments, all, a substantial portion, a significant portion or a major portion of the third C4 raffinate stream is routed to the metathesis conversion unit 530, and the remainder (if any) is directed to the mixed butanols production zone 550 for production of mixed butanols. In further embodiments, all, a substantial portion, a significant portion or a major portion of the third C4 raffinate stream is routed to the mixed butanols production zone 550 for production of mixed butanols, and the remainder (if any) is directed to both the mixed feed steam cracking zone 230 and the metathesis conversion unit 530. In further embodiments, all, a substantial portion, a significant portion or a major portion of the third C4 raffinate stream is routed to the mixed butanols production zone 550 for production of mixed butanols, and the remainder (if any) is directed to the mixed feed steam cracking zone 230. In further embodiments, all, a substantial portion, a significant portion or a major portion of the third C4 raffinate stream is routed to the mixed butanols production zone 550 for production of mixed butanols, and the remainder (if any) is directed to the metathesis conversion unit 530. The quantity can be determined, for instance, based upon demand for ethylene, demand for propylene, demand for mixed butanols, and/or minimum ranges for which the unit is operated depending on design capacity.

Figure 6:
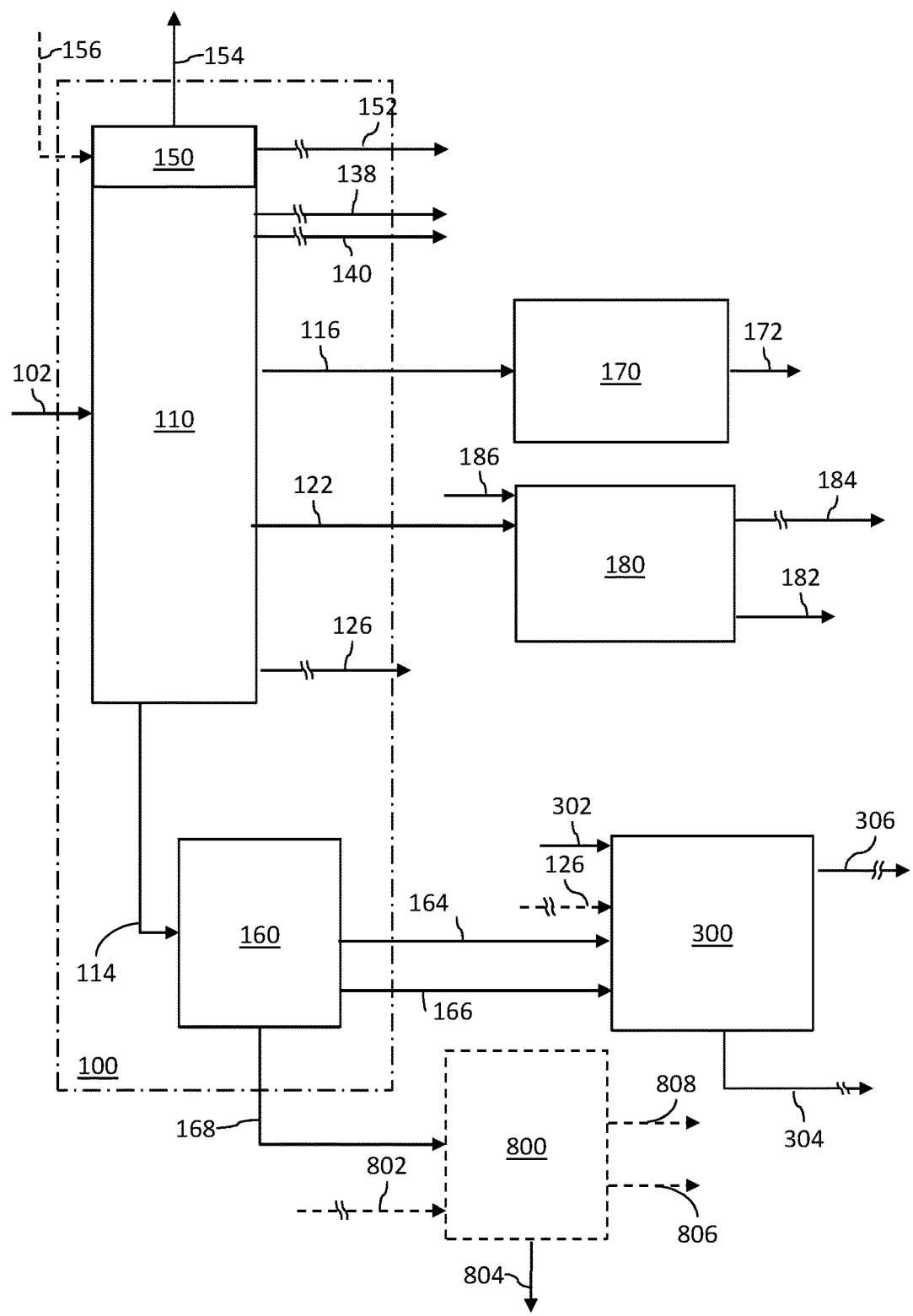
FIGS. 6 and 7 schematically depict operations upstream of a steam cracker complex in further embodiments of processes for producing petrochemicals and fuel product.
Figure 7:
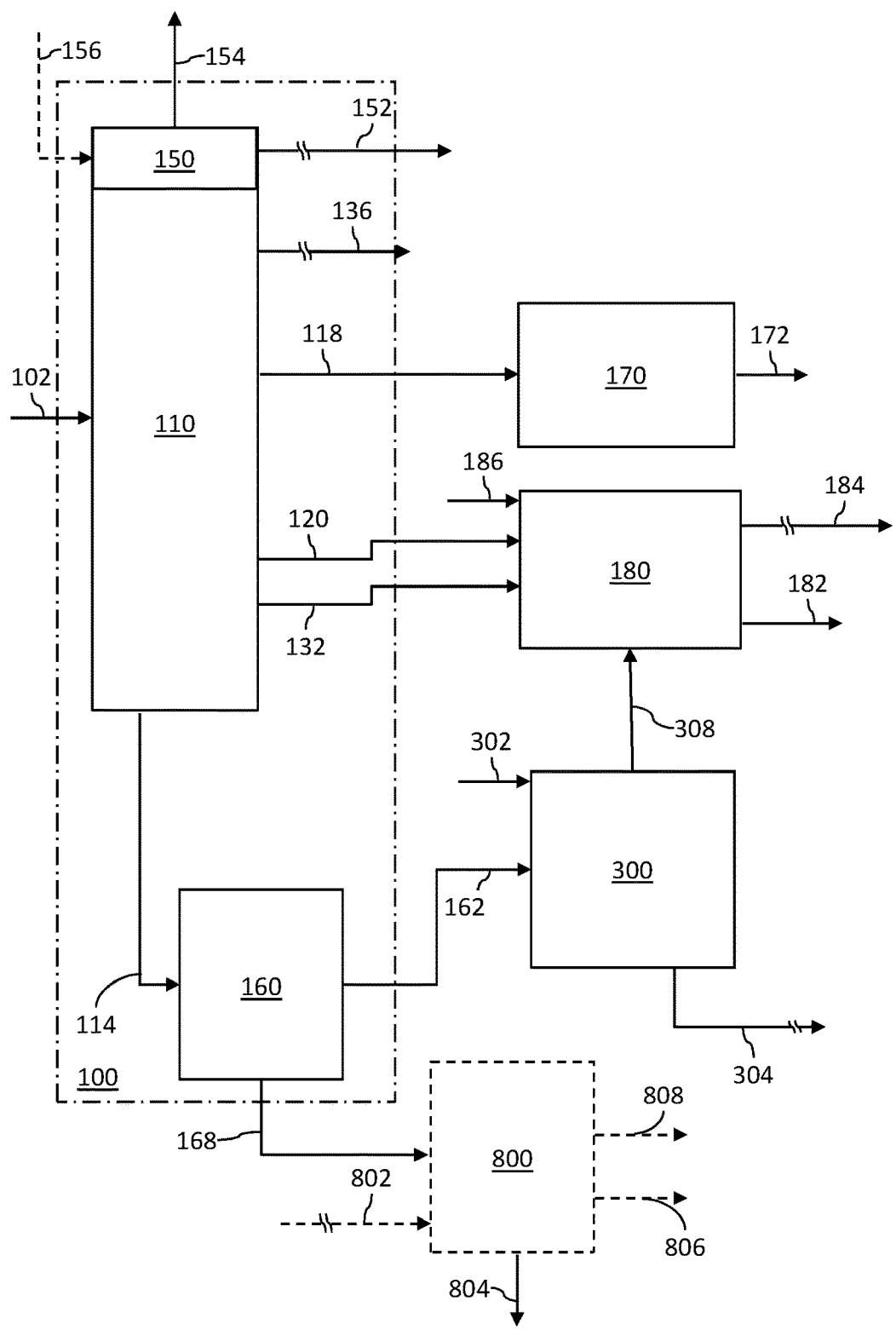
Figure 8:
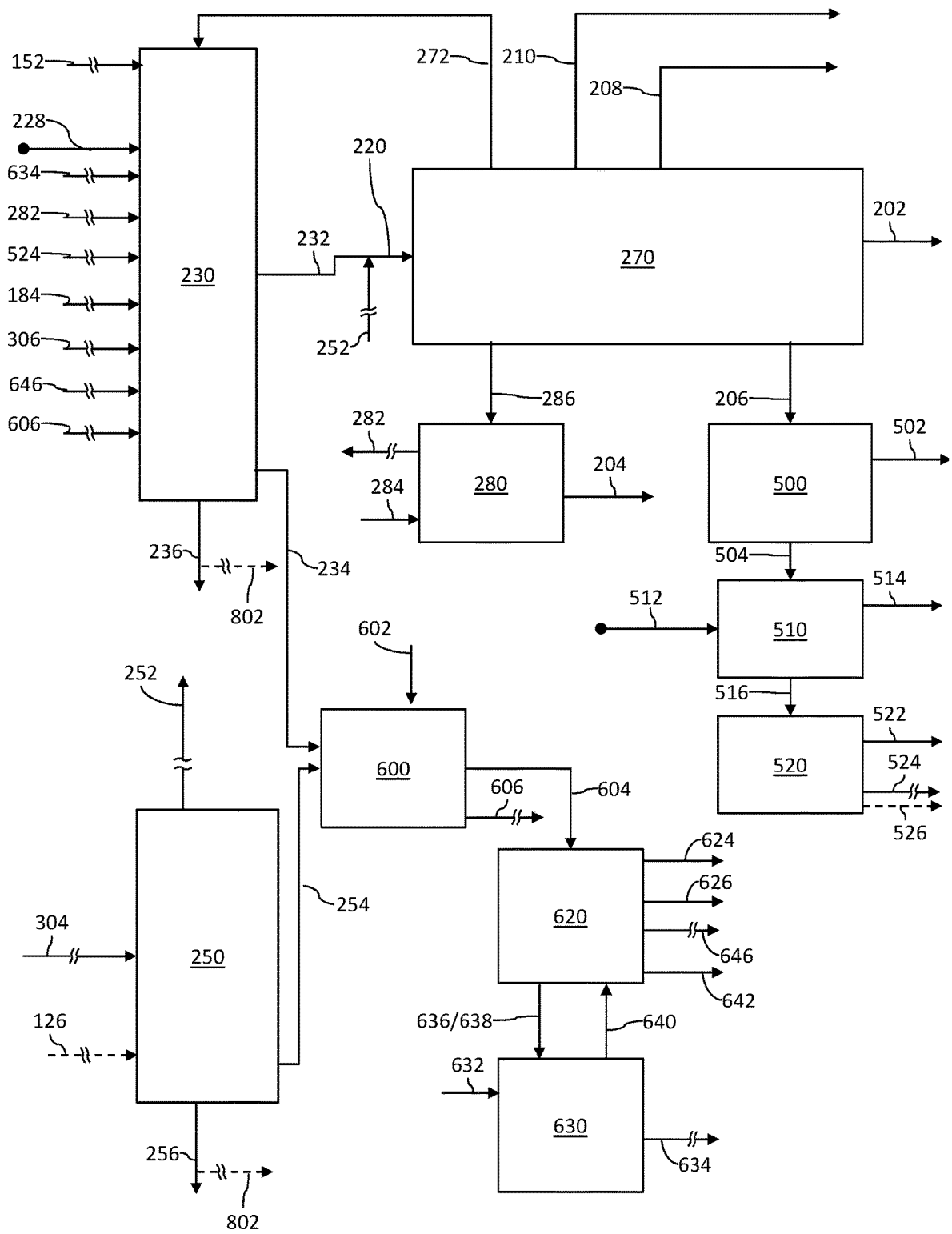
FIG. 8 schematically depicts operations downstream of and including a steam cracker complex in further embodiments of processes for producing petrochemicals and fuel product.

FIGS. 6 and 8 schematically depict embodiments of processes and systems for conversion of crude oil to petrochemicals and fuel products including a mixed feed steam cracking zone 230 and a gas oil steam cracking zone 250. Furthermore, FIG. 7 shows a variant of operations upstream of the steam cracker zones 230 and 250.

A crude oil feed 102 is passed to a crude complex 100, which generally includes an atmospheric distillation zone 110, a saturated gas plant 150 and a vacuum distillation zone 160. The atmospheric distillation unit and vacuum distillation unit are used in well-known arrangements.

Intermediate streams obtained from the feed 102 via separation in the crude complex 100 include: off-gas 154, obtained within the crude complex 100 via the saturated gas plant 150, and the sweet off-gas can be sent to the fuel gas system or to the steam cracker complex; a light ends stream 152, obtained within the crude complex 100 via the saturated gas plant 150, and which is passed to the mixed feed steam cracking zone 230; one or more straight run naphtha stream(s), in this embodiment a light naphtha stream 138 and a heavy naphtha stream 140, which are passed to the mixed feed steam cracking zone 230; a first middle distillate stream 116 that is passed to a kerosene sweetening zone 170, such as a mercaptan oxidation zone; a second middle distillate stream 122 that is passed to a diesel hydrotreating zone 180; a third middle distillate stream 126 that can be passed to the gas oil hydrotreating zone 300, the gas oil steam cracking zone 250, or both the gas oil hydrotreating zone 300 and the gas oil steam cracking zone 250; an atmospheric residue fraction 114 that is passed to the vacuum distillation zone 160; a light vacuum gas oil stream 164 and a heavy vacuum gas oil stream 166 from the vacuum distillation zone 160 that are passed to the vacuum gas oil hydrotreating zone 300; and a vacuum residue stream 168 from the vacuum distillation zone 160, all or a portion of which can optionally be passed to a residue treating zone 800, and/or to a fuel oil pool. In certain embodiments the third middle distillate stream 126 is routed to both the gas oil hydrotreating zone 300 and the gas oil steam cracking zone 250. For instance, the third middle distillate stream 126 can be two separate temperature fractions of an atmospheric gas oil stream from the crude complex 100, including heavy AGO that is passed to the gas oil hydrotreating zone 300, and medium AGO (if not contained in the second middle distillate fraction 122) that bypasses the gas oil hydrotreating zone 300 and is directly routed to the gas oil steam cracking zone 250 without hydrotreating. In another arrangement, the third middle distillate stream 126 can be divided based on volume or mass flow, for instance, with a diverter.

The intermediate streams from the crude complex 100 are used in an efficient manner in the integrated process and system herein. The light ends stream 152, a portion of the straight run naphtha stream(s), in this embodiment a light naphtha stream 138 and a heavy naphtha stream 140, are routed to the mixed feed steam cracking zone 230 as feed for conversion into light olefins and other valuable petrochemicals. Either or both of the straight run naphtha streams, light naphtha 138 and heavy naphtha 140, can optionally be steam-stripped in a side stripper prior to routing to the mixed feed steam cracking zone 230.

Components of the crude complex not shown but which are well-known can include feed/product and pump-around heat exchangers, crude charge heaters, crude tower(s), product strippers, cooling systems, hot and cold overhead drum systems including re-contactors and off-gas compressors, and units for water washing of overhead condensing systems. The atmospheric distillation zone 110 can include well-known design features. Furthermore, in certain embodiments, all or portions of the naphtha, kerosene and atmospheric gas oil products from the atmospheric distillation column are steam-stripped in side strippers, and atmospheric residue is steam-stripped in a reduced-size can section inside the bottom of the atmospheric distillation column.

The feed to the atmospheric distillation zone 110 is primarily the crude feed 102, although it shall be appreciated that wild naphtha, LPGs and off-gas streams from the diesel hydrotreating zone 180, the vacuum gas oil hydrotreating zone 300, and in certain embodiments from an optional residue treating zone, can be routed to the atmospheric distillation zone 110 where they are fractionated before being passed to the cracking complex. A desalting unit (not shown) is typically included upstream of the distillation zone 110. A substantial amount of the water required for desalting can be obtained from a sour water stripper within the integrated process and system.

The desalting unit refers to a well-known arrangement of vessels for desalting of crude oil, and as used herein is operated to reduce the salt content to a target level, for instance, to a level of less than or equal to about 10, 5, or 3 wppm. In certain embodiments two or more desalters are included to achieve a target salt content of less than or equal to about 3 wppm.

In one embodiment of a crude complex 100 herein, feed 102 is preheated before entering a desalting unit, for instance, to a temperature (° C.) in the range of about 105-165, 105-150, 105-145, 120-165, 120-150, 120-145, 125-165, 125-150, 125-145, and in certain embodiments about 135. Suitable desalters are designed to remove salt down to a typical level of about 0.00285 kg/m$^3$ (1 lb/1000 bbl) in a single stage. In certain embodiments, plural preheat and desalting trains are employed. The desalter operating pressure can be based on a pressure margin above crude and water mixture vapor pressure at desalter operating temperature to ensure liquid phase operation, for instance in the range of about 2.75-4.15, 2.75-3.80, 2.75-3.65, 3.10-4.15, 3.10-3.80, 3.10-3.65, 3.25-4.15, 3.25-3.80, 3.25-3.65 and in certain embodiments about 3.45 barg.

The atmospheric distillation zone 110 can employ fractionated products and pumparounds to provide enough heat for desalting. In certain embodiments, the desalter operating temperature can be controlled by a diesel pumparound swing heat exchanger. In certain embodiments, desalter brine preheats desalter make-up water in a spiral type heat exchanger to minimize fouling and achieve rundown cooling against cooling water before the brine is routed to the wastewater system.

In certain embodiments, desalted crude is preheated before entering a preflash tower, to a temperature (° C.) in the range of about 180-201, 185-196, or 189-192. The preflash tower removes LPG and light naphtha from the crude before it enters the final preheat exchangers. The preflash tower minimizes the operating pressure of the preheat train to maintain liquid phase operation at the crude furnace pass valves and also reduces the requisite size of the main crude column.

In one example of a suitable crude distillation system, a crude furnace vaporizes materials at or below a certain cut point, for instance, at a temperature (° C.) in the range of about 350-370, 355-365 or 360 (680° F.), before the crude enters the flash zone of the crude tower. The furnace is designed for a suitable outlet temperature, for instance, at a temperature (° C.) in the range of about 338-362, 344-354 or 348.9 (660° F.). Crude column flash zone conditions are at a temperature (° C.) in the range about 328-374, 328-355, 337-374, 327-355, or 346.1 (655° F.), and a pressure (barg) in the range of about 1.35-1.70, 1.35-1.60, 1.44-1.70, 1.44-1.60 or 1.52.

In certain embodiments the crude tower contains 59 trays and produces six cuts, with draw temperatures for each product as follows: light naphtha, 104.4° C. (220° F.) (overhead vapor); heavy naphtha, 160.6° C. (321° F.) (sidedraw); kerosene, 205° C. (401° F.) (sidedraw); diesel, 261.7° C. (503° F.) (sidedraw); AGO, 322.2° C. (612° F.) (sidedraw); atmospheric residue, 340.6° C. (645° F.) (bottoms). The heavy naphtha draw includes a reboiled side stripper against diesel pumparound, and is controlled to a 185° C. (365° F.) D86 end point. The kerosene draw includes a steam stripper at 14.54 kg/m$^3$ (5.1 lb steam per bbl); the draw rate is limited on the back end by freeze point. The diesel draw includes a steam stripper at 14.54 kg/m$^3$ (5.1 lb steam per bbl), and this draw is controlled to a 360° C. (680° F.) D86 95% point. The AGO draw includes a steam stripper at 14.82 kg/m$^3$ (5.2 lb steam per bbl), which sets the overflash at 2 vol % on crude. The crude tower also contains 3 pumparounds for top, diesel, and AGO. Diesel pumparound provides heat to the heavy naphtha stripper reboiler and debutanizer reboiler along with controlling desalter operating temperature via swing heat. The bottoms stream of the atmospheric column is steam stripped at 28.5 kg/m$^3$ (10 lb steam/bbl).

The atmospheric residue fraction 114 from the atmospheric distillation zone 110 is further distilled in the vacuum distillation zone 160, which fractionates the atmospheric residue fraction 114 into vacuum gas oil fractions, shown as a light vacuum gas oil stream 164 and a heavy vacuum gas oil stream 166, and a vacuum residue stream 168. Vacuum gas oil from streams 164 and 166 is routed to the vacuum gas oil hydrotreating zone 300. The vacuum residue stream 168 can be routed to a fuel oil pool (such as a high sulfur fuel oil pool), or in certain embodiments, passed to a residue treating zone 800.

The vacuum distillation zone 160 can include well-known design features, such as operation at reduced pressure levels (mm Hg absolute pressure), for instance, in the range of about 30-40, 32-36 or 34, which can be maintained by steam ejectors or mechanical vacuum pumps. Vacuum bottoms can be quenched to minimize coking, for instance, via exchange against crude at a temperature (° C.) in the range of about 334-352, 334-371, 338-352, 338-371 or 343.3 (650° F.). Vacuum distillation can be accomplished in a single stage or in plural stages. In certain embodiments, the atmospheric residue fraction 114 is heated in a direct fired furnace and charged to vacuum fractionator at a temperature (° C.) in the range of about 390-436, 390-446, 380-436, 380-446 or 400-425.

In one embodiment, the atmospheric residue is heated to a temperature (° C.) in the range of about 399-420, 399-430, 389-420, 389-430 or 409.4 (769° F.) in the vacuum furnace to achieve flash zone conditions of a temperature (° C.) in the range of about 392-412, 392-422, 382-412, 382-422 or 401.7 (755° F.) and pressure levels (mm Hg absolute pressure) in the range of about 30-40, 32-36 or 34. The vacuum column is designed for a theoretical cut point temperature (° C.) in the range of about 524-551, 524-565, 511-551, 511-565 or 537.8 (1000° F.), by removing light VGO and heavy VGO from the vacuum residue. The overhead vacuum system can include two parallel trains of jet ejectors each including three jets. A common vacuum pump is used at the final stage. In one embodiment, the vacuum tower is sized for a 0.35 C-Factor and about a 14.68 lpm/m$^2$ (0.3 gpm/ft$^2$) wetting rate at the bottom of the wash zone. Wash zone slop wax is recycled to the vacuum furnace to minimize fuel oil production. Vacuum bottoms are quenched via exchange against crude to minimize coking at a temperature (° C.) in the range of about 334-352, 334-371, 338-352, 338-371 or 343.3° C. (650° F.).

The saturated gas plant 150 generally comprises a series of operations including fractionation and in certain systems absorption and fractionation, as is well known, with an objective to process light ends to separate fuel gas range components from LPG range components suitable as a steam cracker feedstock. The light ends that are processed in one or more saturated gas plants within embodiments of the integrated system and process herein are derived from the crude distillation, such as light ends and LPG. In addition, other light products can optionally be routed to the saturated gas plant 150, shown in dashed lines as stream 156, such as light gases from refinery units within the integrated system, and in certain embodiments light gases from outside of the battery limits. For instance, stream 156 can contain off-gases and light ends from the diesel hydrotreating zone 180, the gas oil hydrotreating zone 300 and/or the py-gas hydrotreating zone 600. The products from the saturated gas plant 150 include: an off-gas stream 154, containing C1-C2 alkanes that is passed to the fuel gas system and/or the steam cracker complex; and a light ends stream 152, containing C2+, that is passed to the mixed feed steam cracking unit 230.

In certain embodiments, a suitable saturated gas plant 150 includes amine and caustic washing of liquid feed, and amine treatment of vapor feed, before subsequent steps. The crude tower overhead vapor is compressed and recontacted with naphtha before entering an amine scrubber for H$_2$S removal and is then routed to the steam cracker complex. Recontact naphtha is debutanized to remove LPGs which are amine washed and routed to the steam cracker complex. The debutanized naphtha is routed separately from the heavy naphtha to the steam cracker complex. As is known, light naphtha absorbs C4 and heavier hydrocarbons from the vapor as it travels upward through an absorber/debutanizer. Off-gas from the absorber/debutanizer is compressed and sent to a refinery fuel gas system. A debutanizer bottoms stream is sent to the mixed feed steam cracker as an additional source of feed.

As shown, the first middle distillate fraction 116 is processed in a kerosene sweetening zone 170 to remove unwanted sulfur compounds, as is well-known. Treated kerosene is recovered as a kerosene fuel product 172, for instance, jet fuel compliant with Jet A or Jet A-1 specifications, and optionally other fuel products. In certain embodiments herein, all or a portion of the first middle distillate fraction 116 is not used for fuel production, but rather is used as a feed for distillate hydroprocessing so as to produce additional feed for the mixed feed steam cracking zone 230.

For instance, a suitable kerosene sweetening zone 170 can include, but is not limited to, systems based on Merox™ technology (Honeywell UOP, US), Sweetn'K technology (Axens, IFP Group Technologies, FR) or Thiolex™ technology (Merichem Company, US). Processes of these types are well-established commercially and appropriate operating conditions are well known to produce kerosene fuel product 172 and disulfide oils as by-products. In certain kerosene sweetening technologies impregnated carbon is utilized as catalyst to promote conversion to disulfide oil. In certain embodiments, common treatment of sour water from the kerosene sweetening zone 170 and other unit operations is employed to maximize process integration.

For example, one arrangement of a kerosene sweetening zone includes caustic wash of the kerosene feed for residual H$_2$S removal, employing an electrostatic coalescer (for instance using 10 degrees Baumé). The reactor vessel containing an effective quantity of activated carbon catalyst utilizes air in conjunction with the caustic solution to affect the oxidation of mercaptan to disulfides. Caustic is separated from treated kerosene in the bottom section of the reactor. After water washing, kerosene product passes upwards through one of two parallel salt filters to remove free water and some soluble water. The kerosene product passes downward through one of two parallel clay filters for removal of solids, moisture, emulsions and surfactants, so as to ensure that the kerosene product meets haze, color stability and water separation specifications, for instance, compliant with Jet A specifications.

The second middle distillate fraction 122 is processed in a diesel hydrotreating zone 180 in the presence of an effective amount of hydrogen obtained from recycle within the diesel hydrotreating zone 180 and make-up hydrogen 186. In certain embodiments, all or a portion of the make-up hydrogen 186 is derived from the steam cracker hydrogen stream 210 from the olefins recovery train 270. A suitable hydrotreating zone 180 can include, but is not limited to, systems based on technology commercially available from Honeywell UOP, US; Chevron Lummus Global LLC (CLG), US; Axens, IFP Group Technologies, FR; Haldor Topsoe A/S, DK; or joint technology from KBR, Inc, US, and Shell Global Solutions, US.

The diesel hydrotreating zone 180 operates under conditions effective for removal of a significant amount of the sulfur and other known contaminants, for instance, to meet necessary sulfur specifications for the diesel fuel fraction 182, such as diesel fuel compliant with Euro V diesel standards. In addition, a hydrotreated naphtha fraction 184 (sometimes referred to as wild naphtha) is recovered from the diesel hydrotreating zone 180, which is routed to the mixed feed steam cracking zone 230 as one of plural steam cracking feed sources. Effluent off-gases are recovered from the diesel hydrotreating zone 180 and are passed to the olefins recovery train, the saturated gas plant as part of the other gases stream 156, and/or directly to a fuel gas system. Liquefied petroleum gas can be recovered from the diesel hydrotreating zone 180 and routed to the mixed feed steam cracking zone, the olefins recovery train and/or the saturated gas plant. In certain embodiments, the hydrotreated naphtha fraction 184 is routed through the crude complex 100, alone, or in combination with other wild naphtha fractions from within the integrated process. In embodiments in which hydrotreated naphtha fraction 184 is routed through the crude complex 100, all or a portion of the liquefied petroleum gas produced in the diesel hydrotreating zone 180 can be passed with the hydrotreated naphtha fraction 184. In certain embodiments, all, a substantial portion or a significant portion of the wild naphtha 184 is routed to the mixed feed steam cracking zone 230 (directly or through the crude complex 100).

The diesel hydrotreating zone 180 can optionally process other fractions from within the complex (not shown). In embodiments in which a kerosene sweetening zone 170 is used, all or a portion of the disulfide oil can be additional feed to the diesel hydrotreating zone 180. Further, all or a portion of the first middle distillate fraction 116 can be additional feed to the diesel hydrotreating zone 180. Additionally, all or a portion of distillates from the vacuum gas oil hydrotreating zone 300, and/or all or a portion of distillates from the optional vacuum residue treatment zone, can be routed to the diesel hydrotreating zone 180. Any portion of distillates not routed to the diesel hydrotreating zone 180 can be passed to the crude complex 100 or routed to the mixed feed steam cracking zone 230. Further, all or a portion of light pyrolysis oil can be routed to the diesel hydrotreating zone 180.

The diesel hydrotreating zone 180 can contain one or more fixed-bed, ebullated-bed, slurry-bed, moving bed, continuous stirred tank (CSTR) or tubular reactors, in series and/or parallel arrangement. In certain embodiments, the diesel hydrotreating zone 180 contains a layered bed reactor with three catalyst beds and having inter-bed quench gas, and employs a layered catalyst system with the layer of hydrodewaxing catalyst positioned between beds of hydrotreating catalyst. Additional equipment, including exchangers, furnaces, feed pumps, quench pumps, and compressors to feed the reactor(s) and maintain proper operating conditions, are well known and are considered part of the diesel hydrotreating zone 180. In addition, equipment including pumps, compressors, high temperature separation vessels, low temperature separation vessels and the like to separate reaction products and provide hydrogen recycle within the diesel hydrotreating zone 180, are well known and are considered part of the diesel hydrotreating zone 180.

In certain embodiments, the diesel hydrotreating zone 180 operating conditions include:

a reactor inlet temperature (° C.) in the range of from about 296-453, 296-414, 296-395, 336-453, 336-414, 336-395, 355-453, 355-414, 355-395 or 370-380;

a reactor outlet temperature (° C.) in the range of from about 319-487, 319-445, 319-424, 361-487, 361-445, 361-424, 382-487, 382-445, 382-424 or 400-406;

a start of run (SOR) reaction temperature (° C.), as a weighted average bed temperature (WABT), in the range of from about 271-416, 271-379, 271-361, 307-416, 307-379, 307-361, 325-416, 325-379, 325-361 or 340-346;

an end of run (EOR) reaction temperature (° C.), as a WABT, in the range of from about 311-476, 311-434, 311-414, 352-476, 352-434, 352-414, 373-476, 373-434, 373-414 or 390-396;

a reaction inlet pressure (barg) in the range of from about 48-72, 48-66, 48-63, 54-72, 54-66, 54-63, 57-72, 57-66 or 57-63;

a reaction outlet pressure (barg) in the range of from about 44-66, 44-60, 44-58, 49-66, 49-60, 49-58, 52-66, 52-60 or 52-58;

a hydrogen partial pressure (barg) (outlet) in the range of from about 32-48, 32-44, 32-42, 36-48, 36-44, 36-42, 38-48, 38-44 or 38-42;

a hydrogen treat gas feed rate (standard liters per liter of hydrocarbon feed, SLt/Lt) up to about 400, 385, 353 or 337, in certain embodiments from about 256-385, 256-353, 256-337, 289-385, 289-353, 289-337, 305-385, 305-353 or 305-337;

a hydrogen quench gas feed rate (SLt/Lt) up to about 100, 85, 78 or 75, in certain embodiments from about 57-85, 57-78, 57-75, 64-85, 64-78, 64-75, 68-85, 68-78 or 68-75;

and a make-up hydrogen feed rate (SLt/Lt) up to about 110, 108, 100 or 95, in certain embodiments from about 70-108, 70-100, 70-95, 80-108, 80-100, 80-95, 85-108, 85-100 or 85-95.

An effective quantity of hydrotreating catalyst is provided in the diesel hydrotreating zone 180, including those possessing hydrotreating functionality and which generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. The catalyst used in the diesel hydrotreating zone 180 can include one or more catalyst selected from Co/Mo, Ni/Mo, Ni/W, and Co/Ni/Mo. Combinations of one or more of Co/Mo, Ni/Mo, Ni/W and Co/Ni/Mo, can also be used. The combinations can be composed of different particles containing a single active metal species, or particles containing multiple active species. In certain embodiments, Co/Mo hydrodesulfurization catalyst is suitable. Effective liquid hourly space velocity values ($h^{-1}$), on a fresh feed basis relative to the hydrotreating catalysts, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.8-1.2. Suitable hydrotreating catalysts used in the diesel hydrotreating zone 180 have an expected lifetime in the range of about 28-44, 34-44, 28-38 or 34-38 months.

In certain embodiments, an effective quantity of hydrodewaxing catalyst is also added. In such embodiments, effective hydrodewaxing catalysts include those typically used for isomerizing and cracking paraffinic hydrocarbon feeds to improve cold flow properties, such as catalysts comprising Ni, W, or molecular sieves or combinations thereof. Catalyst comprising Ni/W, zeolite with medium or large pore sizes, or a combination thereof are suitable, along with catalyst comprising aluminosilicate molecular sieves such as zeolites with medium or large pore sizes. Effective commercial zeolites include for instance ZSM-5, ZSM-11, ZSM-12, ZSM-22, ZSM-23, ZSM 35, and zeolites of type beta and Y. Hydrodewaxing catalyst is typically supported on an oxide support such as $Al_2O_3$, $SiO_2$, $ZrO_2$, zeolites, zeolite-alumina, alumina-silica, alumina-silica-zeolite, activated carbon, and mixtures thereof. Effective liquid hourly space velocity values ($h^{-1}$), on a fresh feed basis relative to the hydrodewaxing catalyst, are in the range of from about 0.1-12.0, 0.1-8.0, 0.1-4.0, 0.5-12.0, 0.5-8.0, 0.5-4.0, 1.0-12.0, 1.0-8.0, 1.0-4.0 or 1.6-2.4. Suitable hydrodewaxing catalysts used in the diesel hydrotreating zone 180 have an expected lifetime in the range of about 28-44, 34-44, 28-38 or 34-38 months.

In high capacity operations, two or more parallel trains of reactors are utilized. In such embodiments, the flow in the diesel hydrotreating zone 180 is split after the feed pump into parallel trains, wherein each train contains feed/effluent heat exchangers, feed heater, a reactor and the hot separator. Each reactor contains three catalyst beds with inter-bed quench gas. A layered catalyst system is used with the layer of hydrodewaxing catalyst positioned between beds of hydrotreating catalyst. The trains recombine after the hot separators. Tops from the hot separators are combined and passed to a cold separator. Bottoms from the hot separators and from the cold separator are passed to a product stripper to produce stabilized ultra-low sulfur diesel and wild naphtha. Tops from the cold separator are subjected to absorption and amine scrubbing. Recycle hydrogen is recovered, and passed (along with make-up hydrogen) to the reaction zone as treat gas and quench gas.

The light vacuum gas oil stream 164 and heavy vacuum gas oil stream 166 (or full range VGO, not shown) are processed in a gas oil hydrotreating zone 300 in the presence of an effective amount of hydrogen obtained from recycle within the gas oil hydrotreating zone 300 and make-up hydrogen 302. In certain embodiments, all or a portion of the make-up hydrogen 302 is derived from the steam cracker hydrogen stream 210 from the olefins recovery train 270. In certain embodiments (shown in dashed lines in FIG. 6), all or a portion of the heavy middle distillate fraction, such as a portion of the third middle distillate fraction 126 as atmospheric gas oil from the atmospheric distillation zone 110, can be treated in the gas oil hydrotreating zone. The heavy middle distillate fraction can include a full range atmospheric gas oil, or a fraction thereof such as heavy atmospheric gas oil. Further, a portion of the third middle distillate fraction 126 can be routed to the gas oil hydrotreating zone 300, while the remainder bypasses gas oil hydrotreating zone 300 and is routed directly to the gas oil steam cracking zone 250 without hydrotreating.

In certain embodiments, all, a substantial portion, a significant portion or a major portion of the combined vacuum gas oil, streams 164 and 166, is routed to the vacuum gas oil hydrotreating zone 300; the remainder of vacuum gas oil (if any) can be routed directly to the gas oil steam cracking zone 250, bypassing the vacuum gas oil hydrotreating zone.

In accordance with the process herein, the severity of the gas oil hydrotreating operation can be used to moderate the relative yield of olefin and aromatic chemicals from the overall complex and improve the economic threshold of cracking heavy feeds. This application of a gas oil hydrotreating zone. as a chemical yield control mechanism, is uncommon in the industry, where fuels products are typically the product objectives.

The gas oil hydrotreating zone 300 operates under suitable hydrotreating conditions, and generally produces off-gas and light ends (not shown), a wild naphtha stream 306 and hydrotreated gas oil stream 304. Effluent off-gases are recovered from the gas oil hydrotreating zone 300 and are passed to the olefins recovery train, the saturated gas plant as part of the other gases stream 156, and/or directly to a fuel gas system. Liquefied petroleum gas can be recovered from the gas oil hydrotreating zone 300 and routed to the mixed feed steam cracking zone, the olefins recovery train and/or the saturated gas plant. The naphtha fraction 306 is routed to the mixed feed steam cracking zone 230. In certain embodiments, the hydrotreated naphtha fraction 306 is routed through the crude complex 100, alone, or in combination with other wild naphtha fractions from within the integrated process. In embodiments in which hydrotreated naphtha fraction 306 is routed through the crude complex 100, all or a portion of the liquefied petroleum gas produced in the gas oil hydrotreating zone 300 can be passed with the hydrotreated naphtha fraction 306. Hydrotreated gas oil 304 is routed to the gas oil steam cracking zone 250. In certain embodiments, as shown in FIG. 7 described below, in addition to or in conjunction with the hydrotreated naphtha fraction 306, all or a portion of the hydrotreated distillates and naphtha from the gas oil hydrotreating zone 300 are passed to the diesel hydrotreating zone 180.

The gas oil hydrotreating zone 300 can operate under mild, moderate or severe conditions, depending on factors including the feedstock and the desired degree of conversion. Such conditions are effective for removal of a significant amount of the sulfur and other known contaminants, and for conversion of the feed(s) into a major proportion of hydrotreated gas oil 304 that is passed to the gas oil steam cracking zone 250, and minor proportions of off-gases, light ends, and hydrotreated naphtha 306 that is routed to the mixed feed steam cracking zone 230 (optionally via the crude complex 100). The hydrotreated gas oil fraction 304 generally contains the portion of the gas oil hydrotreating zone 300 effluent that is at or above the AGO, H-AGO or VGO range.

For instance, a suitable gas oil hydrotreating zone 300 can include, but is not limited to, systems based on technology commercially available from Honeywell UOP, US; Chevron Lummus Global LLC (CLG), US; Axens, IFP Group Technologies, FR; or Shell Global Solutions, US.

The gas oil hydrotreating zone 300 can contain one or more fixed-bed, ebullated-bed, slurry-bed, moving bed, continuous stirred tank (CSTR) or tubular reactors, in series and/or parallel arrangement. Additional equipment, including exchangers, furnaces, feed pumps, quench pumps, and compressors to feed the reactor(s) and maintain proper operating conditions, are well known and are considered part of the gas oil hydrotreating zone 300. In addition, equipment, including pumps, compressors, high temperature separation vessels, low temperature separation vessels and the like to separate reaction products and provide hydrogen recycle within the gas oil hydrotreating zone 300, are well known and are considered part of the gas oil hydrotreating zone 300.

An effective quantity of catalyst is provided in gas oil hydrotreating zone 300, including those possessing hydrotreating functionality, for hydrodesulfurization and hydrodenitrification. Such catalyst generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. In certain embodiments, the catalyst used in the gas oil hydrotreating zone 300 includes one or more beds selected from Co/Mo, Ni/Mo, Ni/W, and Co/Ni/Mo. Combinations of one or more beds of Co/Mo, Ni/Mo, Ni/W and Co/Ni/Mo, can also be used. The combinations can be composed of different particles containing a single active metal species, or particles containing multiple active species. In certain embodiments, a combination of Co/Mo catalyst and Ni/Mo catalyst are effective for hydrodesulfurization and hydrodenitrification. One or more series of reactors can be provided, with different catalysts in the different reactors of each series. For instance, a first reactor includes Co/Mo catalyst and a second reactor includes Ni/Mo catalyst. Suitable catalyst used in the gas oil hydrotreating zone 300 have an expected lifetime in the range of about 28-44, 28-38, 34-44 or 34-38 months.

In certain embodiments, the gas oil hydrotreating zone 300 operating conditions include:

a reactor inlet temperature (° C.) in the range of from about 324-496, 324-453, 324-431, 367-496, 367-453, 367-431, 389-496, 389-453, 389-431 or 406-414;

a reactor outlet temperature (° C.) in the range of from about 338-516, 338-471, 338-449, 382-516, 382-471, 382-449, 404-516, 404-471, 404-449 or 422-430;

a start of run (SOR) reaction temperature (° C.), as a weighted average bed temperature (WABT), in the range of from about 302-462, 302-422, 302-402, 342-462, 342-422, 342-402, 362-462, 362-422, 362-402 or 378-384;

an end of run (EOR) reaction temperature (° C.), as a WABT, in the range of from about 333-509, 333-465, 333-443, 377-509, 377-465, 377-443, 399-509, 399-465, 399-443 or 416-424;

a reaction inlet pressure (barg) in the range of from about 91-137, 91-125, 91-119, 102-137, 102-125, 102-119, 108-137, 108-125, 108-119 or 110-116;

a reaction outlet pressure (barg) in the range of from about 85-127, 85-117, 85-111, 96-127, 96-117, 96-111, 100-127, 100-117 or 100-111;

a hydrogen partial pressure (barg) (outlet) in the range of from about 63-95, 63-87, 63-83, 71-95, 71-87, 71-83, 75-95, 75-87, 75-83 or 77-81;

a hydrogen treat gas feed rate (SLt/Lt) up to about 525, 510, 465 or 445, in certain embodiments from about 335-510, 335-465, 335-445, 380-510, 380-465, 380-445, 400-510, 400-465 or 400-445;

a hydrogen quench gas feed rate (SLt/Lt) up to about 450, 430, 392 or 375, in certain embodiments from about 285-430, 285-392, 285-375, 320-430, 320-392, 320-375, 338-430, 338-392 or 338-375;

a make-up hydrogen feed rate (SLt/Lt) up to about 220, 200, 180 or 172, in certain embodiments from about 130-200, 130-180, 130-172, 148-200, 148-180, 148-172, 155-200, 155-180 or 155-172; and liquid hourly space velocity values ($h^{-1}$), on a fresh feed basis relative to the hydrotreating catalysts, in the range of from about 0.1-10.0, 0.1-5.0, 0.1-2.0, 0.3-10.0, 0.3-5.0, 0.3-2.0, 0.4-10.0, 0.4-5.0, 0.4-3.0 or 0.5-2.5.

Under the above conditions and catalyst selections, exemplary products from the gas oil hydrotreating zone 300 include 1-30, 5-30, 2-27 or 5-27 wt % of effluent (relative to the feed to the gas oil hydrotreating zone 300) boiling at or below the atmospheric residue end boiling point, such as 370° C., including LPG, kerosene, naphtha, and atmospheric gas oil range components. The remaining bottoms fraction is the hydrotreated gas oil fraction, all or a portion of which can be effectively integrated as feed to the gas oil steam cracking zone 250 as described herein.

In additional embodiments, the gas oil hydrotreating zone 300 can operate under conditions effective for feed conditioning and to maximize targeted conversion to petrochemicals in the steam cracker complex. Accordingly, in certain embodiments severity conditions are selected that achieve objectives differing from those used for conventional refinery operations. That is, while typical VGO hydrotreating operates with less emphasis on conservation of liquid product yield, in the present embodiment VGO hydrotreating operates to produce a higher yield of lighter products which are intentionally recovered to maximize chemicals yield. In embodiments to maximize conversion to petrochemicals, the gas oil hydrotreating zone 300 operating conditions include:

a reactor inlet temperature (° C.) in the range of from about 461-496, 461-473, 485-496 or 473-485;

a reactor outlet temperature (° C.) in the range of from about 480-516, 480-489, 489-495 or 495-516;

a start of run (SOR) reaction temperature (° C.), as a weighted average bed temperature (WABT), in the range of from about 430-462, 430-440, 440-450 or 450-462;

an end of run (EOR) reaction temperature (° C.), as a WABT, in the range of from about 473-509, 484-495, 473-484 or 495-509;

a reaction inlet pressure (barg) in the range of from about 110-137, 113-137, 110-120, 120-129 or 129-137;

a reaction outlet pressure (barg) in the range of from about 104-118, 104-108, 112-118 or 108-112;

a hydrogen partial pressure (barg) (outlet) in the range of from about 76-95, 76-83, 83-89, or 89-95;

a hydrogen treat gas feed rate (SLt/Lt) up to about 525, 485, 490 or 520, in certain embodiments from about 474-520, 474-488, 488-500, or 500-520;

a hydrogen quench gas feed rate (SLt/Lt) up to about 450, 441, 416 or 429, in certain embodiments from about 400-441, 400-415, 415-430, or 430-441;

a make-up hydrogen feed rate (SLt/Lt) up to about 220, 200, 207 or 214, in certain embodiments from about 186-200, 190-200, 186-190, 190-195, or 195-200; and liquid hourly space velocity values ($h^{-1}$), on a fresh feed basis relative to the hydrotreating catalysts, in the range of from about 0.5-0.7, 0.5-0.55, 0.55-0.6, 0.6-0.65, 0.65-0.7.

Under the above conditions and catalyst selections, exemplary products from the gas oil hydrotreating zone 300 operating under conditions effective for feed conditioning and to maximize targeted conversion to petrochemicals in the steam cracker complex include 20-30, 22-28, 23-27 or 24-26 wt % of effluent (relative to the feed to the gas oil hydrotreating zone 300) boiling at or below the atmospheric residue end boiling point, such as 370° C., including LPG, kerosene, naphtha, and atmospheric gas oil range components. The remaining bottoms fraction is the hydrotreated gas oil fraction, all or a portion of which can be effectively integrated as feed to the gas oil steam cracking zone 250 as described herein.

In certain embodiments, the gas oil hydrotreating zone 300 contains one or more trains of reactors, with a first reactor having two catalyst beds with two quench streams including an inter-bed quench stream, and a second reactor (lag reactor) having one catalyst bed with a quench stream. In high capacity operations, two or more parallel trains of reactors are utilized. In such embodiments, the flow in gas oil hydrotreating zone 300 is split after the feed pump into parallel trains, wherein each train contains feed/effluent heat exchangers, feed heater, a reactor and the hot separator. The trains recombine after the hot separators. Tops from the hot separators are combined and passed to a cold separator. Bottoms from the hot separators are passed to a hot flash drum. Bottoms from the cold separator and tops from the hot flash drum are passed to a low pressure flash drum to remove off-gases. Hot flash liquid bottoms and low pressure flash bottoms are passed to a stripper to recover hydrotreated gas oil and wild naphtha. Tops from the cold separator are subjected to absorption and amine scrubbing. Recycle hydrogen is recovered, and passed (along with make-up hydrogen) to the reaction zone as treat gas and quench gas.

In certain embodiments, 0-100 wt % of the vacuum residue stream 168 can be processed in a residue treatment center 800 (shown in dashed lines as an optional embodiment). In additional embodiments, 0-100 wt % of the pyrolysis oil from the steam cracker complex can be routed to the residue treatment center 800. The residue treatment center 800 can include, but is not limited to, one or more of: a catalytic hydrogen addition process, such as a residue hydrocracking system; a thermal coking process, such as a delayed coker; and/or a solvent deasphalting process. In certain embodiments, the residue treatment center 800 produces one or more of a distillate fraction 808, a heavy fraction 806, and/or a bottoms fraction 804. The distillate fraction 808 can include, for instance, one or more middle distillate streams boiling in the temperature range including and below atmospheric gas oil range fractions (for instance in the temperature range of 36-370° C.), or including and below medium atmospheric gas oil range fractions. Note that when the residue treatment center 800 is solvent deasphalting, a distillate fraction 808 is not produced. Portions of the distillate fraction 808 can be used as feed to the mixed feed steam cracking zone 230, feed to one or more of the integrated hydroprocessing zones, and/or used for production of fuel components. All or a portion of the heavy fraction 806 can include, for instance, one or more streams of treated heavy range hydrocarbons boiling above the atmospheric gas oil range (for instance 370° C.), or above the medium atmospheric gas oil range; or deasphalted oil in a solvent deasphalting unit. Portions of the heavy fraction 806 can be used as feed to the gas oil steam cracking zone 250, feed to one or more of the integrated hydroprocessing zones, recovered as unconverted oil product, used for lube oil production in a base oil production zone, and/or incorporated in a fuel oil pool. The bottoms fraction 804 can include, for instance, pitch in a residue hydrocracking system, petroleum coke in a delayed coker, or asphalt in a solvent deasphalting unit).

Embodiments of systems and processes incorporating certain vacuum residue hydroprocessing zones are disclosed in U.S. patent application Ser. No. 15/817,133 filed on Nov. 17, 2017, entitled "Process and System for Conversion of Crude Oil to Petrochemicals and Fuel Products Integrating Vacuum Residue Hydroprocessing," and U.S. patent application Ser. No. 15/817,136 filed on Nov. 17, 2017, entitled "Process and System for Conversion of Crude Oil to Petrochemicals and Fuel Products Integrating Vacuum Residue Conditioning and Base Oil Production," which are commonly owned and are incorporated by reference herein in their entireties. Embodiments of systems and processes incorporating solvent deasphalting are disclosed in U.S. patent application Ser. No. 15/817,140 filed on Nov. 17, 2017, entitled "Process and System for Conversion of Crude Oil to Petrochemicals and Fuel Products Integrating Solvent Deasphalting of Vacuum Residue," which is commonly owned and is incorporated by reference herein in its entirety. Embodiments of systems and processes incorporating thermal coking are disclosed in U.S. patent application Ser. No. 15/817,143 filed on Nov. 17, 2017, entitled "Process and System for Conversion of Crude Oil to Petrochemicals and Fuel Products Integrating Delayed Coking of Vacuum Residue," which is commonly owned and is incorporated by reference herein in its entirety.

The mixed feed steam cracking zone 230, which operates as high severity or low severity thermal cracking process, generally converts LPG, naphtha and heavier hydrocarbons primarily into a mixed product stream 232 containing mixed C1-C4 paraffins and olefins. In certain embodiments, the mixed feed steam cracking zone 230 processes straight-run liquids from the crude unit, ethane and/or propane (from outside battery limits and/or recycled) and various recycle streams from chemical production and recovery areas within the integrated process and system. A suitable mixed feed steam cracking zone 230 can include, but is not limited to, systems based on technology commercially available from Linde AG, DE; TechnipFMC plc, UK; Chicago Bridge & Iron Company N.V. (CB&I), NL; or KBR, Inc, US.

For instance, plural feeds to the mixed feed steam cracking zone 230 include: light ends 152, light naphtha 138 and heavy naphtha 140 (or a full range straight run naphtha 136 as shown in other embodiments) from the crude complex 100; a LPG stream 634 from a transalkylation zone 630, a recycle stream 282 from the methylacetylene/propadiene (MAPD) saturation and propylene recovery zone 280 described below; C4 raffinate 524 from the 1-butene recovery zone 520 described below; wild naphtha 184 from the diesel hydrotreating zone 180 described above (in certain embodiments via the crude complex); hydrotreated naphtha 306 from the gas oil hydrotreating zone 300 described above (in certain embodiments via the crude complex); a raffinate stream 646 from the aromatics extraction zone 620 described below; in certain embodiments a C5 cut derived from the pyrolysis gasoline described below; and optionally, propane stream 228 (from outside battery limits). In certain embodiments, the mixed feed steam cracking zone 230 can accept alternate feeds from other sources, for instance, other naphtha range feeds that may become available from outside of the battery limits.

The products from the mixed feed steam cracking zone 230 include: a quenched cracked gas stream 232 containing mixed C1-C4 paraffins and olefins that is routed to the olefins recovery zone 270; a raw pyrolysis gasoline stream 234 that is routed to a py-gas hydrotreating zone 600 to produce hydrotreated pyrolysis gasoline 604 as feed to the aromatics extraction zone 620, and C5s 606; and a pyrolysis fuel oil stream 236.

The mixed feed steam cracking zone 230 operates under parameters effective to crack the feed into desired products including ethylene, propylene, butadiene, and mixed butenes. Pyrolysis gasoline and pyrolysis oil are also recovered. In certain embodiments, the steam cracking furnace(s) are operated at conditions effective to produce an effluent having a propylene-to-ethylene weight ratio of from about 0.3-0.8, 0.3-0.6, 0.4-0.8 or 0.4-0.6.

The mixed feed steam cracking zone 230 generally comprises one or more trains of furnaces. For instance, a typical arrangement includes reactors that can operate based on well-known steam pyrolysis methods, that is, charging the thermal cracking feed to a convection section in the presence of steam to raise the temperature of the feedstock, and passing the heated feed to the pyrolysis reactor containing furnace tubes for cracking. In the convection section, the mixture is heated to a predetermined temperature, for example, using one or more waste heat streams or other suitable heating arrangement.

The feed mixture is heated to a high temperature in a convection section and material with a boiling point below a predetermined temperature is vaporized. The heated mixture (in certain embodiments along with additional steam) is passed to the pyrolysis section operating at a further elevated temperature for short residence times, such as 1-2 seconds or less, effectuating pyrolysis to produce a mixed product stream. In certain embodiments separate convection and radiant sections are used for different incoming feeds to the mixed feed steam cracking zone 230 with conditions in each optimized for the particular feed.

In certain embodiments, steam cracking in the mixed feed steam cracking zone 230 is carried out using the following conditions: a temperature (° C.) in the convection section in the range of about 400-600, 400-550, 450-600 or 500-600; a pressure (barg) in the convection section in the range of about 4.3-4.8, 4.3-4.45, 4.3-4.6, 4.45-4.8, 4.45-4.6 or 4.6-4.8; a temperature (° C.) in the pyrolysis section in the range of about 700-950, 700-900, 700-850, 750-950, 750-900 or 750-850; a pressure (barg) in the pyrolysis section in the range of about 1.0-1.4, 1.0-1.25, 1.25-1.4, 1.0-1.15, 1.15-1.4 or 1.15-1.25; a steam-to-hydrocarbon ratio in the in the convection section in the range of about 0.3:1-2:1, 0.3:1-1.5:1, 0.5:1-2:1, 0.5:1-1.5:1, 0.7:1-2:1, 0.7:1-1.5:1, 1:1-2:1 or 1:1-1.5:1; and a residence time (seconds) in the pyrolysis section in the range of about 0.05-1.2, 0.05-1, 0.1-1.2, 0.1-1, 0.2-1.2, 0.2-1, 0.5-1.2 or 0.5-1.

In operation of the mixed feed steam cracking zone 230, effluent from the cracking furnaces is quenched, for instance, using transfer line exchangers, and passed to a quench tower. The light products, quenched cracked gas stream 232, are routed to the olefins recovery zone 270. Heavier products are separated in a hot distillation section. A raw pyrolysis gasoline stream is recovered in the quench system. Pyrolysis oil 236 is separated at a primary fractionator tower before the quench tower.

In operation of one embodiment of the mixed feed steam cracking zone 230, the feedstocks are mixed with dilution steam to reduce hydrocarbon partial pressure and then are preheated. The preheated feeds are fed to tubular reactors mounted in the radiant sections of the cracking furnaces. The hydrocarbons undergo free-radical pyrolysis reactions to form light olefins ethylene and propylene, and other by-products. In certain embodiments, dedicated cracking furnaces are provided with cracking tube geometries optimized for each of the main feedstock types, including ethane, propane, and butanes/naphtha. Less valuable hydrocarbons, such as ethane, propane, C4 raffinate, and aromatics raffinate, produced within the integrated system and process, are recycled to extinction in the mixed feed steam cracking zone 230.

In certain embodiments, cracked gas from the furnaces is cooled in transfer line exchangers (quench coolers), for example, producing 1800 psig steam suitable as dilution steam. Quenched cracked gas enters a primary fractionator associated with the mixed feed steam cracking zone 230 for removal of pyrolysis fuel oil bottoms from lighter components. The primary fractionator enables efficient recovery of pyrolysis fuel oil. Pyrolysis fuel oil is stripped with steam in a fuel oil stripper to control product vapor pressure, and cooled. In addition, secondary quench can be carried out by direct injection of pyrolysis fuel oil as quench oil into liquid furnace effluents. The stripped and cooled pyrolysis fuel oil can be sent to a fuel oil pool or product storage. The primary fractionator overhead is sent to a quench water tower; condensed dilution steam for process water treating, and raw pyrolysis gasoline, are recovered. Quench water tower overhead is sent to the olefins recovery zone 270, particularly the first compression stage. Raw pyrolysis gasoline is sent to a gasoline stabilizer to remove any light ends and to control vapor pressure in downstream pyrolysis gasoline processing. A closed-loop dilution steam/process water system is enabled, in which dilution steam is generated using heat recovery from the primary fractionator quench pumparound loops. The primary fractionator enables efficient recovery of pyrolysis fuel oil due to energy integration and pyrolysis fuel oil content in the light fraction stream.

The gas oil steam cracking zone 250 is operated under conditions effective for conversion its feeds into light olefins, pyrolysis gasoline and pyrolysis oil. As described herein feeds to the gas oil steam cracking zone 250 include vacuum gas oil range products from the vacuum gas oil hydroprocessing zone, such as hydrotreated gas oil 304 from the gas oil hydrotreating zone 300, and in certain embodiments all or a portion of the third middle distillate stream 126, for instance, in the atmospheric gas oil range. In certain embodiments, the gas oil steam cracking zone 250 can accept alternate feeds from other sources, for instance, other gas oil range feeds that may become available from outside of the battery limits. Products from the gas oil steam cracking zone 250 include a quenched cracked gas stream 252 containing mixed C1-C4 paraffins and olefins that is routed to the olefins recovery zone 270, a raw pyrolysis gasoline stream 254 that is routed to a py-gas hydrotreating zone 600 to provide additional feed 604 to the aromatics extraction zone 620, and a pyrolysis fuel oil stream 256.

The gas oil steam cracking zone 250 operates under parameters effective to crack the feed into desired products including ethylene, propylene, butadiene, and mixed butenes. Pyrolysis gasoline and pyrolysis oil are also recovered. In certain embodiments, the steam cracking furnace(s) in the gas oil steam cracking zone 250 are operated at conditions effective to produce an effluent having a propylene-to-ethylene weight ratio of from about 0.3-0.8, 0.3-0.6, 0.4-0.8 or 0.4-0.6.

In one embodiment of the gas oil steam cracking zone 250, hydrotreated VGO feedstock is preheated and mixed with dilution steam to reduce hydrocarbon partial pressure in a convection section. The steam-hydrocarbon mixture is heated further and fed to tubular reactors mounted in the radiant sections of the cracking furnaces. The hydrocarbons undergo free-radical pyrolysis reactions to form light olefins, ethylene and propylene, and other by-products.

In certain embodiments, steam cracking in the gas oil steam cracking zone 250 is carried out using the following conditions: a temperature (° C.) in the convection section in the range of about 300-450 or 300-400; a pressure (barg) in the convection section in the range of about 7.2-9.7, 7.2-8.5, 7.2-7.7, 7.7-8.5, 7.7-9.7 or 8.5-9.7; a temperature (° C.) in the pyrolysis section in the range of about 700-850, 700-800, 700-820, 750-850, 750-800 or 750-820; a pressure (barg) in the pyrolysis section in the range of about 0.9-1.2, 0.9-1.4, 0.9-1.6, 1.2-1.4, 1.2-1.6 or 1.4-1.6; a steam-to-hydrocarbon ratio in the in the convection section in the range of about 0.75:1-2:1, 0.75:1-1.5:1, 0.85:1-2:1, 0.9:1-1.5:1, 0.9:1-2:1, 1:1-2:1 or 1:1-1.5:1; and a residence time (seconds) in the pyrolysis section in the range of about 0.02-1, 0.02-0.08, 0.02-0.5, 0.1-1, 0.1-0.5, 0.2-0.5, 0.2-1, or 0.5-1.

In certain embodiments, cracked gas from the gas oil steam cracking zone 250 furnaces is quenched in transfer line exchangers by producing, for instance, 1800 psig steam. Quenched gases are stripped with steam in a primary fractionator. Lighter gases are recovered as the overhead product; a side-draw stream contains pyrolysis fuel oil. The primary fractionator bottoms product is pyrolysis tar, which is cooled and sent to product storage. Pyrolysis fuel oil from the primary fractionator is stripped with steam in the pyrolysis fuel oil stripper, which separates pyrolysis gasoline as the overhead and pyrolysis fuel oil as the bottoms product. Gasoline in the primary fractionator overhead is condensed and combined with gasoline from the pyrolysis fuel oil stripper before being sent to a gasoline stabilizer. The gasoline stabilizer removes light products in the overhead, while the stabilizer bottoms are sent to the py-gas hydrotreater. C4 and lighter gases in the primary fractionator overhead are compressed, for instance, in two stages of compression, before entering an absorber, depropanizer and debutanizer.

Compression of C4 and lighter gases from both the mixed feed steam cracking zone 230 and the gas oil steam cracking zone 250 can be carried out in certain embodiments in a common step, to reduce capital and operating costs associated with compression, thereby increasing efficiencies in the integrated process herein. Accordingly, both the C4 and lighter gas stream 232 and the C4 and lighter gas stream 252 are passed to the olefins recovery zone 270.

In certain embodiments, cracked gas from the furnaces of both the mixed feed steam cracking zone 230 and the gas oil steam cracking zone 250 are subjected to common steps for quenching, recovery of pyrolysis gasoline, recovery of pyrolysis oil, and recovery of C4 and lighter gases. For instance, in one embodiment, the cracked gas from the furnaces of both steam cracking zones are combined cooled in transfer line exchangers (quench coolers), for example, producing 1800 psig steam suitable as dilution steam. Quenched cracked gas enters a primary fractionator for removal of pyrolysis fuel oil bottoms from lighter components. The primary fractionator enables efficient recovery of pyrolysis fuel oil. Pyrolysis fuel oil is stripped with steam in a fuel oil stripper to control product vapor pressure and cooled. In addition, secondary quench can be carried out by direct injection of pyrolysis fuel oil as quench oil into liquid furnace effluents. The stripped and cooled pyrolysis fuel oil can be sent to a fuel oil pool or product storage. The primary fractionator overhead is sent to a quench water tower; condensed dilution steam for process water treating, and raw pyrolysis gasoline, are recovered. Quench water tower overhead is sent to the olefins recovery zone 270, particularly the first compression stage. Raw pyrolysis gasoline is sent to a gasoline stabilizer to remove any light ends and to control vapor pressure in downstream pyrolysis gasoline processing. A closed-loop dilution steam/process water system is enabled, in which dilution steam is generated using heat recovery from the primary fractionator quench pumparound loops. The primary fractionator enables efficient recovery of pyrolysis fuel oil due to energy integration and pyrolysis fuel oil content in the light fraction stream.

The mixed product stream 232 effluent from the mixed feed steam cracking zone 230 and the mixed product stream 252 effluent from the gas oil steam cracking zone 250 shown as combined streams 220. Stream 220 is routed to an olefins recovery zone 270. For instance, light products from the quenching step, C4-, $H_2$ and $H_2S$, are contained in the mixed product stream 220 that is routed to the olefins recovery zone 270. Products include: hydrogen 210 that is used for recycle and/or passed to users; fuel gas 208 that is passed to a fuel gas system; ethane 272 that is recycled to the mixed feed steam cracking zone 230; ethylene 202 that is recovered as product; a mixed C3 stream 286 that is passed to a methyl acetylene/propadiene saturation and propylene recovery zone 280; and a mixed C4 stream 206 that is passed to a butadiene extraction zone 500.

The olefins recovery zone 270 operates to produce on-specification light olefin (ethylene and propylene) products from the mixed product stream 220. For instance, cooled gas intermediate products from the steam cracker is fed to a cracked gas compressor, caustic wash zone, and one or more separation trains for separating products by distillation. In certain embodiments two trains are provided. The distillation train includes a cold distillation section, wherein lighter products such as methane, hydrogen, ethylene, and ethane are separated in a cryogenic distillation/separation operation. The mixed C2 stream from the steam cracker contains acetylenes that are hydrogenated to produce ethylene in an acetylene selective hydrogenation unit. This system can also include ethylene, propane and/or propylene refrigeration facilities to enable cryogenic distillation.

In one embodiment, mixed product stream 232 effluent from the mixed feed steam cracking zone 230 and the mixed product stream 252 effluent from the gas oil steam cracking zone 250 are passed through three to five stages of compression. Acid gases are removed with caustic in a caustic wash tower. After an additional stage of compression and drying, light cracked gases are chilled and routed to a depropanizer. In certain embodiments light cracked gases are chilled with a cascaded two-level refrigeration system (propylene, mixed binary refrigerant) for cryogenic separation. A front-end depropanizer optimizes the chilling train and demethanizer loading. The depropanizer separates C3 and lighter cracked gases as an overhead stream, with C4s and heavier hydrocarbons as the bottoms stream. The depropanizer bottoms are routed to the debutanizer, which recovers a crude C4s stream 206 and any trace pyrolysis gasoline, which can be routed to the py-gas hydrotreating zone 600 (not shown).

The depropanizer overhead passes through a series of acetylene conversion reactors, and is then fed to the demethanizer chilling train, which separates a hydrogen-rich product via a hydrogen purification system, such as pressure swing adsorption. Front-end acetylene hydrogenation is implemented to optimize temperature control, minimize green oil formation and simplify ethylene product recovery by eliminating a C2 splitter pasteurization section that is otherwise typically included in product recovery. In addition, hydrogen purification via pressure swing adsorption eliminates the need for a methanation reactor that is otherwise typically included in product recovery.

The demethanizer recovers methane in the overhead for fuel gas, and C2 and heavier gases in the demethanizer bottoms are routed to the deethanizer. The deethanizer separates ethane and ethylene overhead which feeds a C2 splitter. The C2 splitter recovers ethylene product 202, in certain embodiments polymer-grade ethylene product, in the overhead. Ethane 272 from the C2 splitter bottoms is recycled to the mixed feed steam cracking zone 230. Deethanizer bottoms contain C3s from which propylene product 204, in certain embodiments polymer-grade propylene product, is recovered as the overhead of a C3 splitter, with propane 282 from the C3 splitter bottoms recycled to the mixed feed steam cracking zone 230.

A methyl acetylene/propadiene (MAPD) saturation and propylene recovery zone 280 is provided for selective hydrogenation to convert methyl acetylene/propadiene, and to recover propylene from a mixed C3 stream 286 from the olefins recovery zone 270. The mixed C3 286 from the olefins recovery zone 270 contains a sizeable quantity of propadiene and propylene. The methyl acetylene/propadiene saturation and propylene recovery zone 280 enables production of propylene 204, which can be polymer-grade propylene in certain embodiments.

The methyl acetylene/propadiene saturation and propylene recovery zone 280 receives hydrogen 284 and mixed C3 286 from the olefins recovery zone 270. Products from the methyl acetylene/propadiene saturation and propylene recovery zone 280 are propylene 204 which is recovered, and the recycle C3 stream 282 that is routed to the steam cracking zone 230. In certain embodiments, hydrogen 284 to saturate methyl acetylene and propadiene is derived from hydrogen 210 obtained from the olefins recovery zone 270.

A stream 206 containing a mixture of C4s, known as crude C4s, from the olefins recovery zone 270, is routed to a butadiene extraction zone 500 to recover a high purity 1,3-butadiene product 502 from the mixed crude C4s. In certain embodiments (not shown), a step of hydrogenation of the mixed C4 before the butadiene extraction zone 500 can be integrated to remove acetylenic compounds, for instance, with a suitable catalytic hydrogenation process using a fixed bed reactor. 1,3-butadiene 502 is recovered from the hydrogenated mixed C4 stream by extractive distillation using, for instance, n-methyl-pyrrolidone (NMP) or dimethylformamide (DMF) as solvent. The butadiene extraction zone 500 also produces a raffinate stream 504 containing butane/butene, which is passed to a methyl tertiary butyl ether zone 510.

In one embodiment, in operation of the butadiene extraction zone 500, the stream 206 is preheated and vaporized into a first extractive distillation column, for instance having two sections. NMP or DMF solvent separates the 1,3-butadiene from the other C4 components contained in stream 504. Rich solvent is flashed with vapor to a second extractive distillation column that produces a high purity 1,3-butadiene stream as an overhead product. Liquid solvent from the flash and the second distillation column bottoms are routed to a primary solvent recovery column. Bottoms liquid is circulated back to the extractor and overhead liquid is passed to a secondary solvent recovery or solvent polishing column. Vapor overhead from the recovery columns combines with recycle butadiene product into the bottom of the extractor to increase concentration of 1,3-butadiene. The 1,3-butadiene product 502 can be water washed to remove any trace solvent. In certain embodiments, the product purity (wt %) is 97-99.8, 97.5-99.7 or 98-99.6 of 1,3-butadiene; and 94-99, 94.5-98.5 or 95-98 of the 1,3-butadiene content (wt %) of the feed is recovered. In addition to the solvent such as DMF, additive chemicals are blended with the solvent to enhance butadiene recovery. In addition, the extractive distillation column and primary solvent recovery columns are reboiled using high pressure steam (for instance, 600 psig) and circulating hot oil from the aromatics extraction zone 620 as heat exchange fluid.

A methyl tertiary butyl ether zone 510 is integrated to produce methyl tertiary butyl ether 514 and a second C4 raffinate 516 from the first C4 raffinate stream 504. In certain embodiments C4 Raffinate 1 504 is subjected to selective hydrogenation to selectively hydrogenate any remaining dienes and prior to reacting isobutenes with methanol to produce methyl tertiary butyl ether.

Purity specifications for recovery of a 1-butene product stream 522 necessitate that the level of isobutylene in the second C4 raffinate 516 be reduced. In general, the first C4 raffinate stream 504 containing mixed butanes and butenes, and including isobutylene, is passed to the methyl tertiary butyl ether zone 510. Methanol 512 is also added, which reacts with isobutylene and produces methyl tertiary butyl ether 514. For instance, methyl tertiary butyl ether product and methanol are separated in a series of fractionators, and routed to a second reaction stage. Methanol is removed with water wash and a final fractionation stage. Recovered methanol is recycled to the fixed bed downflow dehydrogenation reactors. In certain embodiments described below with respect to FIG. 9, additional isobutylene can be introduced to the methyl tertiary butyl ether zone 510, for instance, derived from a metathesis conversion unit.

In operation of one embodiment of the methyl tertiary butyl ether zone 510, the raffinate stream 504, contains 35-45%, 37-42.5%, 38-41% or 39-40% isobutylene by weight. This component is removed from the C4 raffinate 516 to attain requisite purity specifications, for instance, greater than or equal to 98 wt % for the 1-butene product stream 522 from the butene-1 recovery zone 520. Methanol 512, in certain embodiments high purity methanol having a purity level of greater than or equal to 98 wt % from outside battery limits, and the isobutylene contained in the raffinate stream 504 and in certain embodiments isobutylene 544 from metathesis (shown in dashed lines as an optional feed), react in a primary reactor. In certain embodiments the primary reactor is a fixed bed downflow dehydrogenation reactor and operates for isobutylene conversion in the range of about 70-95%, 75-95%, 85-95% or 90-95% on a weight basis. Effluent from the primary reactor is routed to a reaction column where reactions are completed. In certain embodiments, exothermic heat of the reaction column and the primary reactor can optionally be used to supplement the column reboiler along with provided steam. The reaction column bottoms contains methyl tertiary butyl ether, trace amounts, for instance, less than 2%, of unreacted methanol, and heavy products produced in the primary reactor and reaction column. Reaction column overhead contains unreacted methanol and non-reactive C4 raffinate. This stream is water washed to remove unreacted methanol and is passed to the 1-butene recovery zone 520 as the C4 raffinate 516. Recovered methanol is removed from the wash water in a methanol recovery column and recycled to the primary reactor.

The C4 raffinate stream 516 from the methyl tertiary butyl ether zone 510 is passed to a separation zone 520 for butene-1 recovery. In certain embodiments, upstream of the methyl tertiary butyl ether zone 510, or between the methyl tertiary butyl ether zone 510 and separation zone 520 for butene-1 recovery, a selective hydrogenation zone can also be included (not shown). For instance, in certain embodiments, raffinate from the methyl tertiary butyl ether zone 510 is selectively hydrogenated in a selective hydrogenation unit to produce butene-1. Other co-monomers and paraffins are also co-produced. The selective hydrogenation zone operates in the presence of an effective amount of hydrogen obtained from recycle within the selective hydrogenation zone and make-up hydrogen; in certain embodiments, all or a portion of the make-up hydrogen for the selective hydrogenation zone is derived from the steam cracker hydrogen stream 210 from the olefins recovery train 270. For instance, a suitable selective hydrogenation zone can include, but is not limited to, systems based on technology commercially available from Axens, IFP Group Technologies, FR; Haldor Topsoe A/S, DK; Clariant International Ltd, CH; Chicago Bridge & Iron Company N.V. (CB&I), NL; Honeywell UOP, US; or Shell Global Solutions, US.

For selective recovery of a 1-butene product stream 522, and to recover a recycle stream 524 that is routed to the mixed feed steam cracking zone 230, and/or in certain embodiments described herein routed to a metathesis zone, one or more separation steps are used. For example, 1-butene can be recovered using two separation columns, where the first column recovers olefins from the paraffins and the second column separates 1-butene from the mixture including 2-butene, which is blended with the paraffins from the first column and recycled to the steam cracker as a recycle stream 524.

In certain embodiments, the C4 raffinate stream 516 from the methyl tertiary butyl ether zone 510 is passed to a first splitter, from which from isobutane, 1-butene, and n-butane are separated from heavier C4 components. Isobutane, 1-butene, and n-butane are recovered as overhead, condensed in an air cooler and sent to a second splitter. Bottoms from the first splitter, which contains primarily cis- and trans-2-butene can be added to the recycle stream 524, or in certain embodiments described herein passed to a metathesis unit. In certain arrangements, the first splitter overhead enters the mid-point of the second splitter. Isobutane product 526 can optionally be recovered in the overhead (shown in dashed lines), 1-butene product 522 is recovered as a sidecut, and n-butane is recovered as the bottoms stream. Bottoms from both splitters is recovered as all or a portion of recycle stream 524.

The raw pyrolysis gasoline streams 234 and 254 from the steam crackers are treated and separated into treated naphtha and other fractions. In certain embodiments, all, a substantial portion or a significant portion of the pyrolysis gasoline streams 234 and 254 are passed to the py-gas hydrotreating zone 600. The raw pyrolysis gasoline streams 234 and 254 are processed in a py-gas hydrotreating zone 600 in the presence of an effective amount of hydrogen obtained from recycle within the py-gas hydrotreating zone 600 and make-up hydrogen 602. Effluent fuel gas is recovered and, for instance, passed to a fuel gas system. In certain embodiments, all or a portion of the make-up hydrogen 602 is derived from the steam cracker hydrogen stream 210 from the olefins recovery train 270. For instance, a suitable py-gas hydrotreating zone 600 can include, but is not limited to, systems based on technology commercially available from Honeywell UOP, US; Chevron Lummus Global LLC (CLG), US; Axens, IFP Group Technologies, FR; Haldor Topsoe A/S, DK; or Chicago Bridge & Iron Company N.V. (CB&I), NL.

The py-gas hydrotreating zone 600 is operated under conditions, and utilizes catalyst(s), that can be varied over a relatively wide range. These conditions and catalyst(s) are selected for effective hydrogenation for saturation of certain olefin and diolefin compounds, and if necessary for hydrotreating to remove sulfur and/or nitrogen containing compounds. In certain embodiments, this is carried out in at least two catalytic stages, although other reactor configurations can be utilized. Accordingly, py-gas hydrotreating zone 600 subjects the pyrolysis gasoline streams 234 and 254 to hydrogenation to produce hydrotreated pyrolysis gasoline 604 effective as feed to the aromatics extraction zone 620. Effluent off-gases are recovered from the py-gas hydrotreating zone 600 and are passed to the olefins recovery train, the saturated gas plant as part of the other gases stream 156, and/or directly to a fuel gas system. Liquefied petroleum gas can be recovered from the py-gas hydrotreating zone 600 and routed to the mixed feed steam cracking zone, the olefins recovery train and/or the saturated gas plant.

In the py-gas hydrotreating zone 600, diolefins in the feed and olefins in the C6+ portion of the feed are saturated to produce a naphtha stream 604, a C5+ feed to the aromatics extraction zone. In certain embodiments, a depentanizing step associated with the py-gas hydrotreating zone 600 separates all or a portion of the Cys, for instance, as additional feed 606 to the mixed feed steam cracking zone 230 and/or as feed to a metathesis unit 530 (as shown, for instance, in FIG. 3, FIG. 5 or FIG. 9). In other embodiments, a depentanizing step associated with the aromatics extraction zone 620 separates all or a portion of the C5s from the hydrotreated naphtha stream 604, for instance, as additional feed to the mixed feed steam cracking zone 230 and/or as feed to a metathesis unit 530.

In certain embodiments, pyrolysis gasoline is processed in a first reaction stage for hydrogenation and stabilization. Diolefins are saturated selectively in the first reaction stage, and remaining olefins are saturated in the second reaction stage along with converting feed sulfur into hydrogen sulfide. The pyrolysis gasoline can be treated in a cold hydrotreating unit, therefore reducing the level of aromatics saturation.

In an example of an effective py-gas hydrotreating zone 600, raw pyrolysis gasoline is passed through a coalescer before entering a feed surge drum. The first stage reactor operates in mixed phase and selectively hydrogenates diolefins to mono-olefins and unsaturated aromatics to side-chain saturated aromatics. Pd-based catalyst materials are effective. Two parallel first-stage reactors can be used in certain embodiments to allow for regeneration in a continuous process without shutdown. In certain embodiments, the first-stage reactor contains three catalyst beds with cooled first stage separator liquid recycled as quench material between each bed. First-stage effluent is stabilized and separated in a column operating under slight vacuum to reduce temperature. In certain embodiments C5 from the C6+ is drawn, followed by a deoctanizer to remove C9+ and produce a C6-C8 heart naphtha cut. The column operates under slight vacuum to limit temperature. The first stage product is stripped to remove hydrogen, $H_2S$, and other light ends. In certain embodiments, the stripped first stage product is depentanized to remove cracked C5, for instance, as feed to a metathesis unit. A second stage reactor operates in vapor phase and removes sulfur and saturates olefins. The second stage product is stripped to remove hydrogen, $H_2S$, and other light ends. In certain embodiments, both reactors are multi-bed and use product recycle to control reactor temperature rise.

In certain embodiments, the first reaction stage of the py-gas hydrotreating zone 600 operating conditions include:
a reactor inlet temperature (° C.) in the range of from about 80-135, 80-125, 80-115, 95-135, 95-125, 95-115, 100-135, 100-125, 100-115 or 107-111;
a reactor outlet temperature (° C.) in the range of from about 145-230, 145-206, 145-200, 165-230, 165-206, 165-200, 175-230, 175-206, 175-200 or 184-188;
a start of run (SOR) reaction temperature (° C.), as a weighted average bed temperature (WABT), in the range of from about 75-125, 75-115, 75-110, 90-125, 90-115, 90-110, 95-125, 95-115, 95-110 or 99-104;
an end of run (EOR) reaction temperature (° C.), as a WABT, in the range of from about 124-195, 124-180, 124-170, 140-195, 140-180, 140-170, 150-195, 150-180, 150-170 or 158-163;
a reaction inlet pressure (barg) in the range of from about 25-40, 25-35, 25-33, 28-40, 28-35, 28-33, 30-40, 30-35 or 30-33;
a reaction outlet pressure (barg) in the range of from about 23-35, 23-33, 23-31, 25-35, 25-33, 25-31, 28-35, 28-33 or –28-31;
a hydrogen partial pressure (barg) (outlet) in the range of from about 15-25, 15-22, 15-21, 18-25, 18-22, 18-21, 19-25 or 19-22;
a hydrogen treat gas feed rate (SLt/Lt) up to about 180, 165 or 156, in certain embodiments from about 120-180, 120-165, 120-156, 134-180, 134-165, 134-156, 140-180, 140-165 or 140-156;
a liquid quench feed ratio (Lt quench/Lt feed) up to about 0.8, 0.7, 0.6 or 0.5, and in certain embodiments in the range of from about 0.35-0.6, 0.35-0.55, 0.35-0.5, 0.4-0.6, 0.4-0.55, 0.4-0.5, 0.45-0.6, 0.45-0.55 or 0.45-0.5; and a make-up hydrogen feed rate (SLt/Lt) up to about 60, 55, 47 or 45, in certain embodiments from about 34-55, 34-47, 34-45, 40-55, 40-47, 40-45, 42-55, 42-47 or 42-45.

In certain embodiments, the second reaction stage of the py-gas hydrotreating zone 600 operating conditions include:

a reactor inlet temperature (° C.) in the range of from about 225-350, 225-318, 225-303, 255-350, 255-318, 255-303, 270-350, 270-318, 270-303 or 285-291;

a reactor outlet temperature (° C.) in the range of from about 289-445, 289-405, 289-386, 328-445, 328-405, 328-386, 345-445, 345-405, 345-386 or 364-370;

a start of run (SOR) reaction temperature (° C.), as a weighted average bed temperature (WABT), in the range of from about 217-336, 217-306, 217-291, 245-336, 245-306, 245-291, 260-336, 260-306, 260-291 or 274-280;

an end of run (EOR) reaction temperature (° C.), as a WABT, in the range of from about 325-416, 325-380, 325-362, 305-416, 305-380, 305-362, 325-416, 325-380, 325-362 or 340-346;

a reaction inlet pressure (barg) in the range of from about 25-37, 25-34, 25-32, 28-37, 28-34, 28-32, 29-37, 29-34 or 29-32;

a reaction outlet pressure (barg) in the range of from about 23-35, 23-32, 23-30, 26-35, 26-32, 26-30, 28-35, 28-32 or 28-30;

a hydrogen partial pressure (barg) (outlet) in the range of from about 6-10, 6-9, 7-10 or 7-9;

a hydrogen treat gas feed rate (SLt/Lt) up to about 135, 126, 116 or 110, in certain embodiments from about 84-126, 84-116, 84-110, 95-126, 95-116, 95-110, 100-126, 100-116 or 100-110; and a make-up hydrogen feed rate (SLt/Lt) up to about 30, 27 or 24, in certain embodiments from about 18-30, 18-27, 18-24, 21-30, 21-27, 21-24, 22-30, 22-27 or 22-24.

An effective quantity of catalyst possessing selective hydrogenation functionality is provided, which generally contain one or more active metal component of metals or metal compounds (oxides or sulfides) selected from Co, Mo, Pt, Pd, Fe, or Ni. The active metal component is typically deposited or otherwise incorporated on a support, such as amorphous alumina, amorphous silica alumina, zeolites, or combinations thereof. Exemplary selective hydrogenation catalyst predominantly use Pd as the active metal component on alumina support, including those commercially available under the trade name Olemax® 600 and Olemax® 601. Effective liquid hourly space velocity values ($h^{-1}$), on a fresh feed basis relative to the first stage pyrolysis gasoline reactor catalyst, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.9-1.44. Suitable catalysts used in the first stage pyrolysis gasoline reactor have an expected lifetime in the range of about 18-30, 22-30, 18-26 or 22-26 months.

An effective quantity of second stage pyrolysis gasoline reactor catalyst is provided, including those having hydrogenation functionality and which generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. In certain embodiments, the catalyst used in the first stage pyrolysis gasoline reactor includes one or more catalyst selected from Co/Mo, Ni/Mo, Ni/W, and Co/Ni/Mo. Combinations of one or more of Co/Mo, Ni/Mo, Ni/W and Co/Ni/Mo, can also be used. For example, a combination of catalyst particles commercially available under the trade names Olemax® 806 and Olemax® 807 can be used, with active metal components of Co and Ni/Mo. The combinations can be composed of different particles containing a single active metal species, or particles containing multiple active species. Effective liquid hourly space velocity values ($h^{-1}$), on a fresh feed basis relative to the first stage pyrolysis gasoline reactor catalyst, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.8-1.2. Suitable catalysts used in the second stage pyrolysis gasoline reactor have an expected lifetime in the range of about 18-30, 22-30, 18-26 or 22-26 months.

Hydrotreated pyrolysis gasoline 604 is routed to the aromatics extraction zone 620. In certain embodiments to maximize production of petrochemicals, all, a substantial portion or a significant portion of the hydrotreated pyrolysis gasoline 604 is passed to the aromatics extraction zone 620. In modes of operation in which production of gasoline is the objective some of the hydrotreated pyrolysis gasoline 604 is passed to a gasoline pool (not shown).

The aromatics extraction zone 620 includes, for instance, one or more extractive distillation units, and operates to separate the hydrotreated pyrolysis gasoline into high-purity benzene, toluene, xylenes and C9 aromatics. As depicted in FIG. 8, a benzene stream 624, a mixed xylenes stream 626 and a raffinate stream 646 are recovered from the aromatics extraction zone 620, with the raffinate stream 646 routed to the mixed feed steam cracking zone 230 as additional feed. In addition, a toluene stream 636 and C9+ aromatics stream 638 are passed from the aromatics extraction zone 620 to a toluene and C9+ transalkylation zone 630 for production of additional benzene and xylenes, recycled as stream 640 to the aromatics extraction zone 620. In certain embodiments ethylbenzene can be recovered (not shown). Heavy aromatics 642 are also recovered from the aromatics extraction zone 620.

In certain embodiments of operation of the aromatics extraction zone 620, aromatics are separated from the feed by extractive distillation using, for instance, n-formylmorpholine (NFM), as an extractive solvent. Benzene, toluene, mixed xylenes and C9+ aromatics are separated via distillation. Benzene and mixed xylenes are recovered as product streams 624 and 626, and toluene 636 and C9+ aromatics 638 are sent to the toluene and C9+ transalkylation zone 630. The transalkylation zone product stream 640 containing benzene and mixed xylenes is returned to the recovery section of the aromatics extraction zone 620. A paraffinic raffinate stream 646 is recycled as feed to the mixed feed steam cracking zone 230. In certain embodiments, the paraffinic raffinate stream 646 is in direct fluid communication with the mixed feed steam cracking zone 230, that is, the stream is not subject to further catalytic processing prior to the steam cracking step.

Selection of solvent, operating conditions, and the mechanism of contacting the solvent and feed permit control over the level of aromatic extraction. For instance, suitable solvents include n-formylmorpholine, furfural, N-methyl-2-pyrrolidone, dimethylformamide, dimethylsulfoxide, phenol, nitrobenzene, sulfolanes, acetonitrile, furfural, or glycols, and can be provided in a solvent to oil ratio of up to about 20:1, in certain embodiments up to about 4:1, and in further embodiments up to about 2:1. Suitable glycols include diethylene glycol, ethylene glycol, triethylene glycol, tetraethylene glycol and dipropylene glycol. The extraction solvent can be a pure glycol or a glycol diluted with from about 2-10 wt % water. Suitable sulfolanes include hydrocarbon-substituted sulfolanes (e.g., 3-methyl sulfolane), hydroxy sulfolanes (e.g., 3-sulfolanol and 3-methyl-4-sulfolanol), sulfolanyl ethers (e.g., methyl-3-sulfolanyl ether), and sulfolanyl esters (e.g., 3-sulfolanyl acetate).

The aromatic separation apparatus can operate at a temperature in the range of from about 40-200, 40-150, 60-200, 60-150, 86-200 or 80-150° C. The operating pressure of the aromatic separation apparatus can be in the range of from about 1-20, 1-16, 3-20, 3-16, 5-20 or 5-16 barg. Types of apparatus useful as the aromatic separation apparatus in certain embodiments of the system and process described herein include extractive distillation columns.

In one embodiment of operation of the aromatics extraction zone 620, the feed contains primarily C6+ components, and is fractionated into a "heart cut" of C6-C8, and a heavy C9+ fraction. The C6-C8 cut is routed to the extractive distillation system where aromatics are separated from non-aromatics (saturates) via solvent distillation. The raffinate (non-aromatics) from the C6-C8 is removed and recycled back to the cracking complex as a feedstock. The aromatics are soluble in the solvent and are carried from the bottom of the extractive distillation column to the solvent stripper where they are stripped from the solvent, to recover aromatics extract and lean solvent which is recycled back to the extractive distillation column. The mixed aromatics extract is routed to a series of fractionation columns (a benzene column, a toluene column and a xylene column) where each aromatic species is successively removed, for instance, as benzene stream 624 and mixed xylenes stream 626. The heavy C9+ fraction is further separated into C9 and C10+ material. The toluene and C9 products are routed to the toluene and C9+ transalkylation zone 630 where they are reacted to form additional benzene and mixed xylenes. This stream is recycled back to the fractionation portion of the aromatics extraction zone 620 to recover the benzene and mixed xylenes as well as to recycle the unconverted toluene and C9 aromatics. The transalkylation effluent does not require re-extraction in the solvent distillation section and therefore is routed to the inlet of the benzene column. In certain embodiments toluene can be recycled to extinction, or approaching extinction. C10 and heavier aromatics are removed as product 642. In certain embodiments ethylbenzene can be recovered.

The toluene and C9+ transalkylation zone 630 operates under conditions effective to disproportionate toluene and C9+ aromatics into a mixed stream 640 containing benzene, mixed xylenes and heavy aromatics. Product ratio of benzene and xylene can be adjusted by selection of catalyst, feedstock and operating conditions. The transalkylation zone 630 receives as feed the toluene stream 636 and the C9+ aromatics stream 638 from the aromatics extraction zone 620. A small quantity of hydrogen 632, in certain embodiments which is obtained all or in part from the hydrogen stream 210 derived from the olefins recovery zone 270, is supplied for transalkylation reactions. Side cracking reactions occur producing fuel gas stream, for instance, passed to the fuel gas system, and LPG stream 634 that is recycled to mixed feed steam cracking zone. A small amount, such as 0.5-3 wt % of the total feed to the aromatics extraction, of heavy aromatics are produced due to condensation reactions and are passed to the mixed stream 640 for recovery with other heavy aromatics.

In operation of one embodiment of the toluene and C9+ transalkylation zone 630, toluene and C9 aromatics are reacted with hydrogen under mild conditions to form a mixture of C6-C11 aromatics. The mixed aromatic product stream 640 is recycled back to the aromatics extraction zone 620 where the benzene and mixed xylenes are recovered as products. C7 and C9 aromatics are recycled back as feed to the transalkylation zone 630, and the C10+ fraction is removed from the aromatics extraction zone 620 as heavy aromatics stream 642. The disproportionation reactions occur in the presence of an effective quantity of hydrogen. A minimal amount of hydrogen is consumed by cracking reactions under reactor conditions. Purge gas is recycled back to the cracking complex for component recovery.

In certain embodiments, pyrolysis oil streams 236 and 256 can be blended into the fuel oil pool as a low sulfur component, and/or used as carbon black feedstock. In additional embodiments, either or both of the pyrolysis oil streams 236 and 256 can be fractioned (not shown) into light pyrolysis oil and heavy pyrolysis oil. For instance, light pyrolysis oil can be blended with one or more of the middle distillate streams, so that 0-100% of light pyrolysis oil derived from either or both of the pyrolysis oil streams 236 and 256 is processed to produce diesel fuel product and/or additional feed to the mixed feed steam cracking zone 230. In another embodiment 0-100% of light pyrolysis oil derived from either or both of the pyrolysis oil streams 236 and 256 can be processed in the gas oil hydrotreating zone 300. In certain embodiments, all, a substantial portion, a significant portion or a major portion of light pyrolysis oil can be passed to one or both of the diesel hydrotreating zone 180 and/or the vacuum gas oil hydroprocessing zone; any remainder can be blended into the fuel oil pool. Heavy pyrolysis oil can be blended into the fuel oil pool as a low sulfur component, and/or used as a carbon black feedstock. In further embodiments, 0-100% of light pyrolysis oil and/or 0-100% of heavy pyrolysis oil derived from either or both of the pyrolysis oil streams 236, 256 can be processed in the optional residue treating zone 800. In certain embodiments, all, a substantial portion, a significant portion or a major portion of the pyrolysis oil streams 236, 256 (light and heavy) can be processed in the optional residue treating zone 800.

In an example, and with reference to FIG. 7, variations relative to FIGS. 6 and 8 are depicted. The process of FIG. 7 operates according to the description with respect to FIGS. 6 and 8, or any of the other embodiments herein, in all other aspects. In certain embodiments the process of FIG. 7 is particularly suitable for an AXL crude oil feed.

Light ends and the naphtha are routed straight from the crude unit to the steam cracker. Light kerosene is fed to a mercaptan oxidation unit to be treated and recovered as jet fuel. Heavy kerosene and atmospheric gas oil are passed to a distillates hydrotreating unit, where they are treated and recovered, for instance to be blended as fuel compliant with Euro V diesel standards. Atmospheric residue is passed to a vacuum distillation unit. VGO is passed to a gas oil hydrotreater. Middle distillates from the gas oil hydrotreater are passed to the middle distillates hydrotreater, and the hydrotreated VGO is sent to a VGO steam cracker. Vacuum residue is sent to fuel oil pool. Therefore, as shown in the example of FIG. 7, treatment of middle distillate fractions comprises: routing a light kerosene stream 118 to the kerosene sweetening zone 170; and routing a heavy kerosene stream 120 and an atmospheric gas oil stream 132 to the diesel hydrotreating zone 180.

Also as shown in FIG. 7, a gas oil hydrotreater 300 operates under suitable hydrotreating conditions for treatment of the vacuum gas oil fraction 162 (which in certain embodiments can be separate heavy and light vacuum gas oil stream), and generally produces LPG, cracked products 308 and hydrotreated gas oil 304. Cracked products 308 are routed to the diesel hydrotreating zone 180, and hydrotreated gas oil 304 is routed to the gas oil steam cracking zone 250. Effluent off-gases are recovered from the gas oil hydrotreating zone 300 and are passed to the olefins recovery train, the saturated gas plant as part of the other gases stream 156, and/or directly to a fuel gas system. Liquefied petroleum gas can be recovered from the gas oil hydrotreating zone 300 and routed to the mixed feed steam cracking zone, the olefins recovery train and/or the saturated gas plant. In certain embodiments all or a portion of the liquefied petroleum gas can be routed with the cracked products 308.

The gas oil hydrotreating zone 300 can operate under mild, moderate or severe conditions, depending on factors including the feedstock and the desired degree of conversion. Such conditions are effective for removal of a significant amount of the sulfur and other known contaminants, and for conversion of the VGO 162 feed into a major proportion of hydrotreated gas oil 304 that is passed to the gas oil steam cracking zone 250, and minor proportions of a stream 308 containing hydrotreated distillates and naphtha range products. The hydrotreated gas oil fraction 304 generally contains the portion of the gas oil hydrotreating 300 effluent that is at or above the AGO, H-AGO or VGO range.

Any portion of stream 308 that is not routed to the diesel hydrotreating zone 180 can optionally be passed to the crude complex 100 or routed to the mixed feed steam cracking zone 230. For example, at least 0-100, 50-100, 60-100, 70-100, 80-100, 50-99, 60-99, 70-99 or 80-99 wt % of the total hydrotreated distillates 308 from the vacuum gas oil hydrotreating zone 300 can be routed to the diesel hydrotreating zone 180.

The steam cracker is followed by an olefins recovery train that is followed by a butadiene extraction unit followed by a methyl tertiary butyl ether unit then a selective C4s hydrogenation unit and butane-1 recovery. MAPD (methyl acetylene/propadiene) saturation unit and propylene recovery section take C3s from the olefins recovery section. The pyrolysis gasoline is sent to a py-gas hydrotreater that is followed by an aromatics extraction unit along with a toluene/C9+ aromatics transalkylation unit. The pyrolysis oil is fed to fuel oil pool, or divided into light pyrolysis oil and heavy pyrolysis oil and used as described herein.

Figure 9:
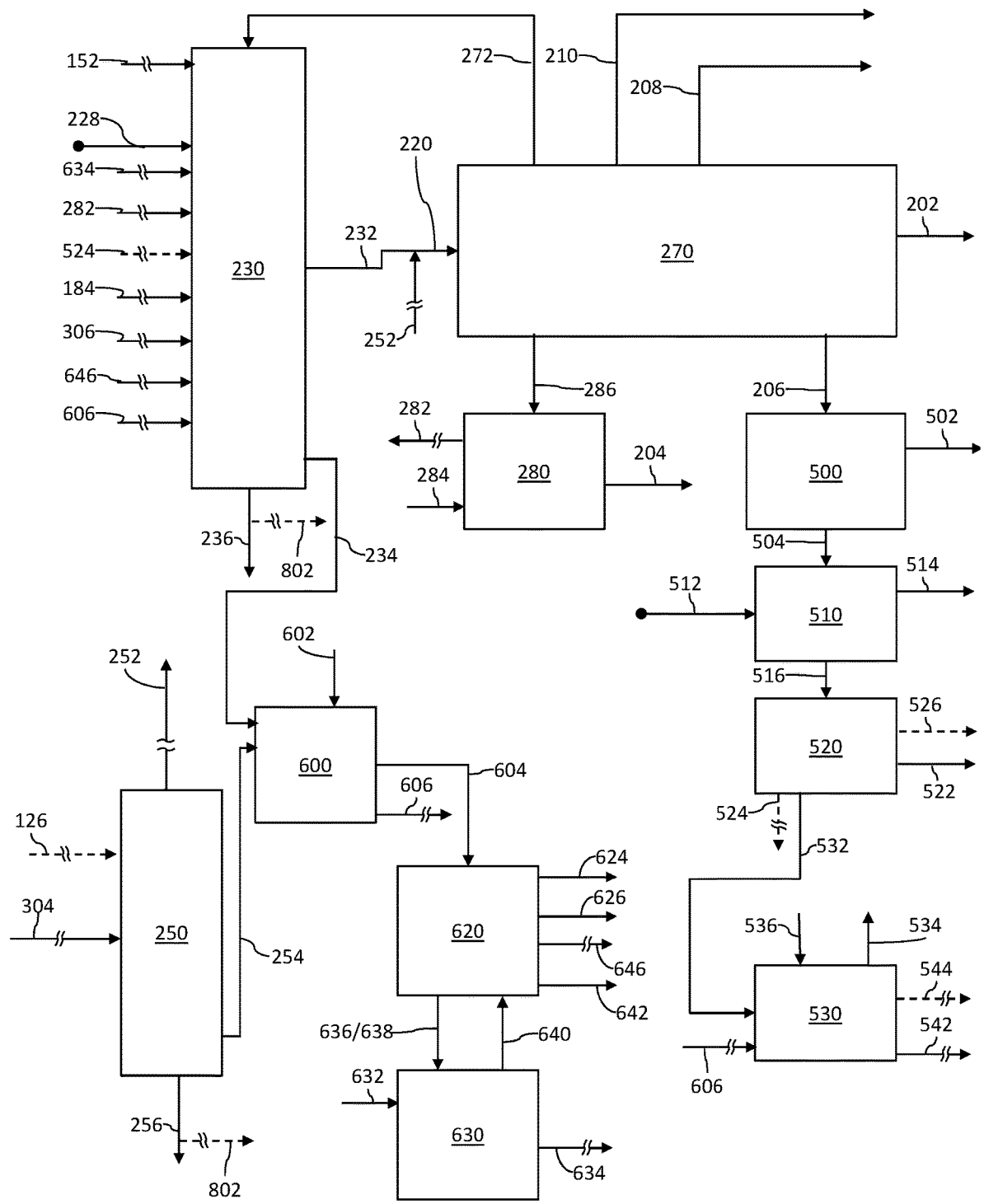
FIG. 9 schematically depicts operations in further embodiments of processes for producing petrochemicals and fuel products integrating metathesis.

FIG. 9 depicts embodiments including integration of a metathesis zone 530. The process of FIG. 9 operates according to the description with respect to FIGS. 6, 7 and 8, or any of the other embodiments herein, in all other aspects. For instance, a suitable metathesis zone 530 can include, but is not limited to, systems based on technology commercially available from Chicago Bridge & Iron Company N.V. (CB&I), NL.

Feedstocks to the metathesis zone 530 include: a portion 536 of the ethylene product 202; a C4 Raffinate-3 stream 532 from the 1-butene recovery zone 520, and the olefinic C5 cut 606 from the py-gas hydrotreating zone 600. The C4 Raffinate-3 stream 532 is 0-100% of the total C4 Raffinate-3 from the 1-butene recovery zone 520; any remaining portion 524 can be recycled to the mixed feed steam cracking zone 230. Products from the metathesis zone 530 include a propylene product stream 534 and a stream 542, having a mixture of mostly saturated C4/C5 from a metathesis unit that is recycled to the mixed feed steam cracking zone. In certain embodiments, isobutylene 544 can also be recovered (shown in dashed lines) and routed to the methyl tertiary butyl ether zone 510. In embodiments that operate without separation of isobutylene, it is included within stream 542.

In an example of a metathesis zone 530 used in the integrated process herein, the C4 Raffinate-3 stream 532 from the separation zone 520 and the C5 olefins stream 606 from the py-gas hydrotreating zone 600 (or the aromatics extraction zone) pass through a guard bed to remove t-butyl catechol and are mixed with a molar excess of fresh and recycled ethylene. The reactor feed passes through another guard bed to remove other trace contaminants, is heated in a furnace and enters the disproportionation (metathesis) reactor, where propylene is formed. The reactions reach equilibrium conversion. The metathesis reactor effluent contains a mixture of propylene, ethylene, and butenes/butanes, and some C5 and heavier components from by-product reactions. C4 olefins isomerize in the disproportionation reactor and react with ethylene to form additional propylene. In certain embodiments, disproportionation of C5 olefins yields isobutylene by-product for production of additional MTBE. Cooled reactor effluent enters a deethylenizer, which recycles overhead ethylene to the disproportionation reactor. Deethylenizer bottoms are passed to a depropylenizer, which recovers grade propylene product as overhead. Propylene product purity is >99.5 mol % (polymer grade). In certain embodiments depropylenizer bottoms enter a deisobutylenizer, which recovers isobutylene as overhead for additional feedstock to the MTBE zone 510. Deisobutylenizer bottoms are mixed with a recycle stream to dilute the olefin concentration, the mixture is heated and mixed with hydrogen, and routed to a total hydrogenation reactor, which saturates any remaining C4/C5 or heavier olefins and thereby enhances light olefin yields. Cooled reactor effluent is recycled as feedstock to the mixed feed steam cracking zone 230.

Figure 10:
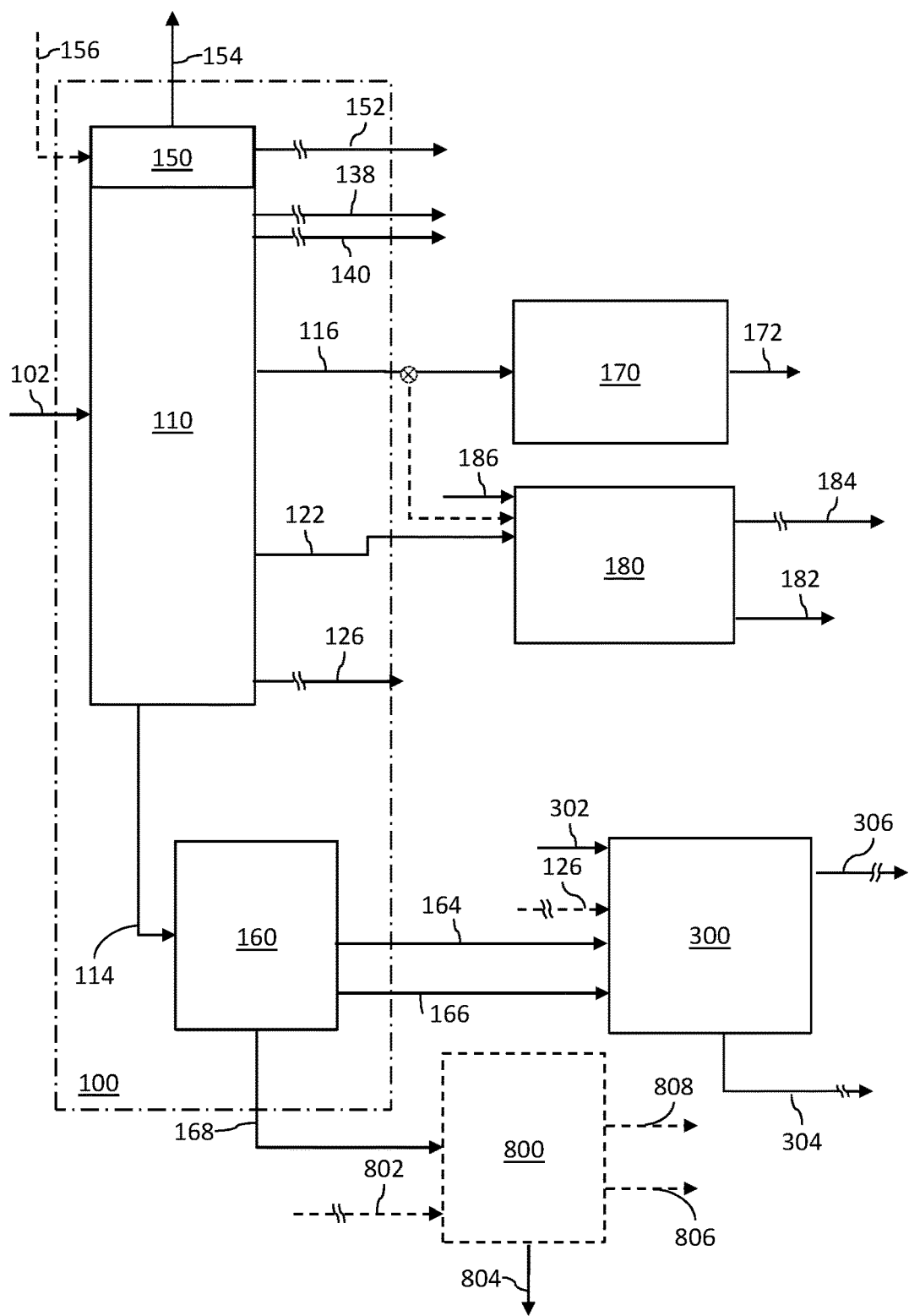
FIGS. 10 and 11 schematically depict operations upstream of a steam cracker complex in still further embodiments of processes for producing petrochemicals and fuel product.

FIG. 10 depicts embodiments in which kerosene sweetening is in an optional unit, that is, the first middle distillate fraction 116 can be routed either through the kerosene sweetening zone 170 or routed to the distillate hydrotreating zone 180. The process of FIG. 10 operates according to the description with respect to FIGS. 6 and 8, or any of the other embodiments herein, in all other aspects.

During periods in which maximizing the kerosene fuel 172 output is desired, the first middle distillate fraction 116 can be routed to the kerosene sweetening zone 170. During periods in which the feedstock to the mixed feed steam cracking zone 230 is to be maximized, the first middle distillate fraction 116 can be routed to the distillate hydrotreating zone 180, so as to produce additional hydrotreated naphtha 184. In additional alternative embodiments, the first middle distillate fraction 116 can be divided (on a volume or weight basis, for example, with a diverter) so that a portion is passed to the distillate hydrotreating zone 180 and the remaining portion is passed to the kerosene sweetening zone 170.

Figure 11:
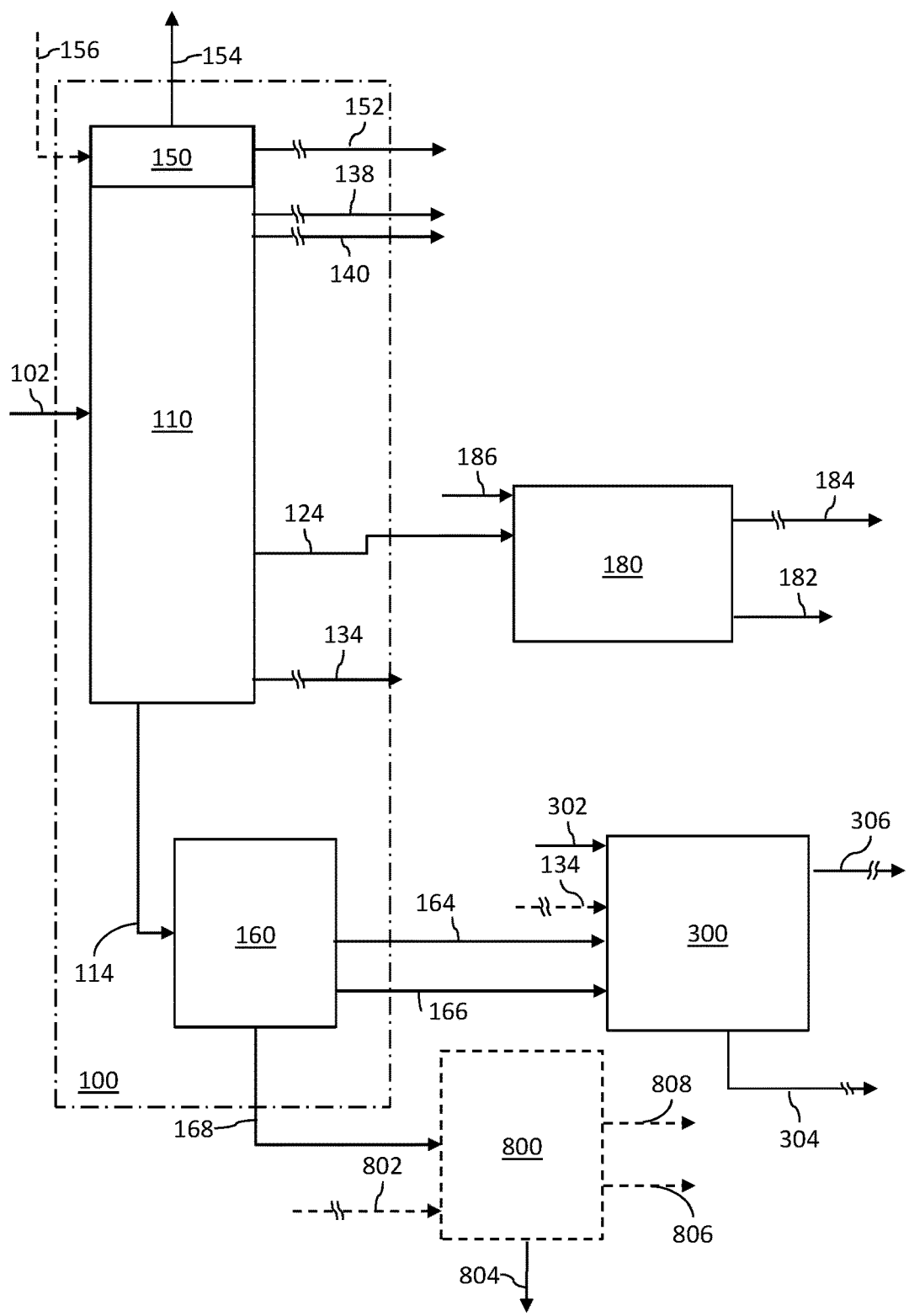

FIG. 11 depicts embodiments in which kerosene sweetening is eliminated.

Accordingly, in the embodiments of FIG. 11, two middle distillate fractions are used. In this embodiment, a first middle distillate fraction 124 is routed to the distillate hydrotreating zone 180, and a second middle distillate fraction 134 may be similar to the third middle distillate fraction 126 described in other embodiments herein. In one example using the arrangement shown in FIG. 11, the first middle distillate fraction 124 contains kerosene range hydrocarbons and medium AGO range hydrocarbons, and the second atmospheric distillation zone middle distillate fraction 134 contains heavy AGO range hydrocarbons. In another example using the arrangement shown in FIG. 11, the first middle distillate fraction 124 contains kerosene range hydrocarbons and a portion of medium AGO range hydrocarbons and the second middle distillate fraction 134 contains a portion of medium AGO range hydrocarbons and heavy AGO range hydrocarbons. The process of FIG. 11 operates according to the description with respect to FIGS. 6, 7 and 9, or any of the other embodiments herein, in all other aspects.

Advantageously, process dynamics of the configurations and the integration of units and streams attain a very high level of integration of utility streams between the mixed feed steam cracking and other process units, result in increased efficiencies and reduced overall operating costs. For instance, the hydrogen can be tightly integrated so that the net hydrogen demand from outside of the battery limits is minimized or even eliminated. In certain embodiments, the overall hydrogen utilization from outside of the battery limits is less than about 40, 30, 15, 10 or 5 wt % hydrogen based on the total hydrogen required by the hydrogen users in the integrated process. Hydrogen is recovered from the olefins recovery train, and is supplied to the hydrogen users in the system, including the diesel hydrotreater, the gas oil hydrotreater, the py-gas hydrotreater, and transalkylation, so as to derive most or all of the utility hydrogen from within the battery limits. In certain embodiments there is zero external hydrogen use, in which make-up hydrogen is only required to initiate the operations; when the reactions reach equilibrium, the hydrogen derived from the mixed feed steam cracking and gas oil steam cracking products provides sufficient hydrogen to maintain the hydrogen requirements of the hydrogen users in the integrated process. In further embodiments, there is a net hydrogen gain, so that hydrogen can be added, for instance, to the fuel gas that is used to operate the various heating units within the integrated process.

Furthermore, the integrated process described herein offers useful outlets for the off-gases and light ends from the hydroprocessing units. For instance, the stream 156 that is passed to the saturated gas plant 150 of the crude complex 100 can contain off-gases and light ends from the hydroprocessing units, such as the diesel hydrotreating zone 180, the gas oil hydrotreating zone 300 and/or from the py-gas hydrotreating zone 600. In other embodiments, in combination with or as an alternative to the passing these off-gases and light ends to stream 156, all or a portion can be routed to the mixed feed steam cracking unit 230. For instance, C2s can be separated from the mixture of methane, hydrogen and C2s using a cold distillation section ("cold box") including cryogenic distillation/separation operations, which can be integrated with any or all of the mixed feed steam cracking unit 230, the saturated gas plant 150 and/or the olefins recovery zone 270. Methane and hydrogen can be passed to a fuel gas system or to an appropriate section of the olefins recovery zone 270, such as the hydrogen purification system. In still further embodiments, in combination with or as an alternative to the passing these off-gases and light ends to stream 156 and/or routing them to the mixed feed steam cracking unit 230, all or a portion can be routed to an appropriate section of the olefins recovery zone 270, such as the depropanizer, or combining the gases with the depropanizer overheads.

The unique configurations presented herein set forth a level of integration, of streams and units that allows the use of gas oil steam crackers in an economically efficient manner. The configurations support and enhance chemical conversion using integrated processes with crude oil as a feed. Hence, not only do these configurations permit lower capital expenditure relative to conventional approaches of chemical production from fuels or refinery by-products, but it also exhibits an economical use of the VGO cracker (through the integration). Accordingly, despite the use of crude oil as the feed, the processes herein are comparable to other options currently common in the industry such as ethane crackers that benefit from availability of ethane as a feed.

Embodiments described herein provide the ability to achieve a crude to chemical conversion ratio in the range of, for instance, up to 80, 50 or 45 wt %, and in certain embodiments in the range of about 39-45 wt %. In certain embodiments the chemical conversion ratio is at least about 39 wt %, and in certain embodiments in the range of about 39-80, 39-50 or, 39-45 wt %. It should be appreciated that this crude to chemicals conversion ratio can vary depending on criteria such as feed, selected technology, catalyst selection and operating conditions for the individual unit operations.

In some embodiments, individual unit operations can include a controller to monitor and adjust the product slate as desired. A controller can direct parameters within any of the individual unit operations the apparatus depending upon the desired operating conditions, which may, for example, be based on customer demand and/or market value. A controller can adjust or regulate valves, feeders or pumps associated with one or more unit operations based upon one or more signals generated by operator data input and/or automatically retrieved data.

Such controllers provide a versatile unit having multiple modes of operation, which can respond to multiple inputs to increase the flexibility of the recovered product. The controller can be implemented using one or more computer systems which can be, for example, a general-purpose computer. Alternatively, the computer system can include specially-programmed, special-purpose hardware, for example, an application-specific integrated circuit (ASIC) or controllers intended for a particular unit operation within a refinery.

The computer system can include one or more processors typically connected to one or more memory devices, which can comprise, for example, any one or more of a disk drive memory, a flash memory device, a RAM memory device, or other device for storing data. The memory is typically used for storing programs and data during operation of the system. For example, the memory can be used for storing historical data relating to the parameters over a period of time, as well as operating data. Software, including programming code that implements embodiments of the invention, can be stored on a computer readable and/or writeable nonvolatile recording medium, and then typically copied into memory wherein it can then be executed by one or more processors. Such programming code can be written in any of a plurality of programming languages or combinations thereof.

Components of the computer system can be coupled by one or more interconnection mechanisms, which can include one or more busses, for instance, between components that are integrated within a same device, and/or a network, for instance, between components that reside on separate discrete devices. The interconnection mechanism typically enables communications, for instance, data and instructions, to be exchanged between components of the system.

The computer system can also include one or more input devices, for example, a keyboard, mouse, trackball, microphone, touch screen, and other man-machine interface devices as well as one or more output devices, for example, a printing device, display screen, or speaker. In addition, the computer system can contain one or more interfaces that can connect the computer system to a communication network, in addition or as an alternative to the network that can be formed by one or more of the components of the system.

According to one or more embodiments of the processes described herein, the one or more input devices can include sensors and/or flow meters for measuring any one or more parameters of the apparatus and/or unit operations thereof. Alternatively, one or more of the sensors, flow meters, pumps, or other components of the apparatus can be connected to a communication network that is operatively coupled to the computer system. Any one or more of the above can be coupled to another computer system or component to communicate with the computer system over one or more communication networks. Such a configuration permits any sensor or signal-generating device to be located at a significant distance from the computer system and/or allow any sensor to be located at a significant distance from any subsystem and/or the controller, while still providing data therebetween. Such communication mechanisms can be affected by utilizing any suitable technique including but not limited to those utilizing wired networks and/or wireless networks and protocols.

Although the computer system is described above by way of example as one type of computer system upon which various aspects of the processes herein can be practiced, it should be appreciated that the invention is not limited to being implemented in software, or on the computer system as exemplarily described. Indeed, rather than implemented on, for example, a general purpose computer system, the controller, or components or subsections thereof, can alternatively be implemented as a dedicated system or as a dedicated programmable logic controller (PLC) or in a distributed control system. Further, it should be appreciated that one or more features or aspects of the processes can be implemented in software, hardware or firmware, or any combination thereof. For example, one or more segments of an algorithm executable by a controller can be performed in separate computers, which in turn, can be in communication through one or more networks.

In some embodiments, one or more sensors and/or flow meters can be included at locations throughout the process, which are in communication with a manual operator or an automated control system to implement a suitable process modification in a programmable logic controlled process. In one embodiment, a process includes a controller which can be any suitable programmed or dedicated computer system, PLC, or distributed control system. The flow rates of certain product streams can be measured, and flow can be redirected as necessary to meet the requisite product slate.

Factors that can result in various adjustments or controls include customer demand of the various hydrocarbon products, market value of the various hydrocarbon products, feedstock properties such as API gravity or heteroatom content, and product quality (for instance, gasoline and middle distillate indicative properties such as octane number for gasoline and cetane number for middle distillates).

The disclosed processes and systems create new outlets for direct conversion of crude oil, for instance, light crudes such as Arab Extra Light (AXL) or Arab Light (AL) crude oil. Additionally, the disclosed processes and systems offer novel configurations that, compared to known processes and systems, requires lower capital expenditure relative to conventional approaches of chemical production from fuels or refinery by-products and that utilize refining units and an integrated chemicals complex. The disclosed processes and systems substantially increase the proportion of crude oil that is converted to high purity chemicals that traditionally command high market prices. Complications resulting from advancing the threshold of commercially proven process capacities are minimized or eliminated using the processes and systems described herein.

The disclosed processes and systems utilize different commercially proven units arranged in novel configurations. These novel configurations enable production of refined products and petrochemical products including olefins, aromatics, MTBE, and butadiene. The disclosed processes and systems allow chemicals producers to de-couple from fuel markets and have more freedom to increase chemical yields as a fraction of crude rate, as compared to traditional chemical production using refinery intermediates or by-products as feedstock. Also, the disclosed processes and systems substantially increase the proportion of crude oil that is converted to high purity chemicals that traditionally command high market prices.

The disclosed processes and systems provide alternatives for chemicals production that have lower capital investment relative to conventional routes that utilize refining units and an integrated chemicals complex. Moreover, the disclosed processes and systems offer the flexibility of simultaneously producing fuel products and chemical products. The ratio of chemicals to residual fuels can be modulated by process operations to address changing fuels and chemical market opportunities. In certain embodiments, the process configurations are flexible to enable processing of crude oil, such as Arab Light or Arab Extra Light, to provide superior production of chemical products, while minimizing the production of refined fuel products. The configurations offer the flexibility to structure operations to adjust the ratio of petrochemicals to refined products in order to achieve optimum operations and allows shifting the production ratio of chemicals to fuels, thereby adjusting to market conditions.

For example, in vacuum gas oil hydroprocessing, as severity increases, the yield of hydrotreated gas oil decreases as the naphtha yield increases, although for the most part the distillate yield does change as much because wild naphtha product is the result of distillate cracking. By modulating severity of vacuum gas oil hydroprocessing, the shift is between naphtha and hydrotreated gas oil relative product rates. The olefin yield of naphtha in the steam cracker is superior to hydrotreated gas oil; while the heavy product yield (mixed C4s and pyrolysis gasoline) from hydrotreated gas oil is superior to naphtha. Therefore, a key advantage of modulating the vacuum gas oil hydroprocessing conversion is to economically and dynamically address changing market conditions for olefin and aromatic products, which may swing dramatically.

Each of the processing units are operated at conditions typical for such units, which conditions can be varied based on the type of feed to maximize, within the capability of the unit's design, the desired products. Desired products can include fractions suitable as feedstock to the mixed feed steam cracking zone 230 or gas oil steam cracking zone 250, or fractions suitable for use as fuel products. Likewise, processing units employ appropriate catalyst(s) depending upon the feed characteristics and the desired products. Certain embodiments of these operating conditions and catalysts are described herein, although it shall be appreciated that variations are well known in the art and are within the capabilities of those skilled in the art.

For the purpose of the simplified schematic illustrations and descriptions herein, accompanying components that are conventional in crude centers, such as the numerous valves, temperature sensors, preheater(s), desalting operation(s), and the like are not shown.

In addition, accompanying components that are in conventional hydroprocessing units such as, for example, hydrogen recycle sub-systems, bleed streams, spent catalyst discharge sub-systems, and catalyst replacement sub-systems the like are not shown.

Further, accompanying components that are in conventional thermal cracking systems such as steam supplies, coke removal sub-systems, pyrolysis sections, convection sections and the like are not shown.

The method and system of the present invention have been described above and in the attached drawings; however, modifications will be apparent to those of ordinary skill in the art and the scope of protection for the invention is to be defined by the claims that follow.

The invention claimed is:

1. An integrated system for producing petrochemicals and fuel products comprising:
    an atmospheric distillation unit (ADU) operable to receive and separate a feed, and discharge a first ADU fraction comprising naphtha, a second ADU fraction comprising at least a portion of middle distillates from the feed, and a third ADU fraction comprising atmospheric residue;
    a vacuum distillation unit (VDU) operable to receive and separate the third ADU fraction, and discharge a first VDU fraction comprising vacuum gas oil;
    a distillate hydroprocessing (DHP) zone operable to receive and convert middle distillates from the second ADU fraction into a first DHP fraction and a second DHP fraction, wherein the first DHP fraction comprises naphtha and the second DHP fraction is used for diesel fuel production;
    a gas oil hydrotreating (GOHT) zone operable to receive and treat vacuum gas oil from the first VDU fraction and produce a first GOHT fraction containing naphtha range components, and a hydrotreated gas oil fraction;
    a steam cracking zone comprising (a) a mixed feed steam cracking (MFSC) zone operable to receive and thermally crack naphtha from the first ADU fraction and a C6-C9 non-aromatics raffinate stream derived from an aromatics extraction zone, and (b) a gas oil steam cracking (GOSC) zone operable to receive and thermally crack the hydrotreated gas oil fraction, wherein the steam cracking zone is operable to produce a mixed product stream containing mixed C1-C4 paraffins and olefins, a pyrolysis gas stream, and a pyrolysis oil stream;
    a naphtha hydrotreating zone operable to receive and treat the pyrolysis gas stream and produce a hydrotreated pyrolysis gas stream; and
    the aromatics extraction zone operable to receive and separate the hydrotreated pyrolysis gas stream into one or more aromatic products streams, and the C6-C9 non-aromatics raffinate stream.

2. The system as in claim 1, wherein the MFSC zone is operable to receive and thermally crack naphtha from the first DHP fraction, naphtha from the first GOHT fraction, or both naphtha from the first DHP fraction and naphtha from the first GOHT fraction.

3. The system as in claim 1, wherein the naphtha hydrotreating zone is operable to produce a C5s stream, and wherein the MFSC zone is operable to receive and thermally crack the C5s stream.

4. The system as in claim 1, wherein the ADU is further operable to receive and separate naphtha from the first DHP fraction, naphtha from the first GOHT fraction, or both naphtha from the first DHP fraction and naphtha from the first GOHT fraction.

5. The system as in claim 1, wherein the ADU is operable to separate a further ADU fraction including heavy AGO that is heavier than the second ADU fraction and lighter than the third ADU fraction, and wherein the GOHT zone is operable to receive and convert the further ADU fraction.

6. The system as in claim 1, wherein the ADU is operable to separate a further ADU fraction including heavy AGO that is heavier than the second ADU fraction and lighter than the third ADU fraction, and wherein the GOSC zone is operable to receive and thermally crack the further ADU fraction.

7. The system as in claim 1, wherein the ADU is operable to separate a further ADU fraction including kerosene that is heavier than the first ADU fraction and lighter than the second ADU fraction, and the system further comprising a kerosene sweetening zone operable to receive and treat the further ADU fraction.

8. The system as in claim 7, wherein the ADU is operable to separate a further ADU fraction including heavy AGO that is heavier than the second ADU fraction and lighter than the third ADU fraction, and wherein (a) the GOSC zone is operable to receive and thermally crack the additional ADU fraction, or (b) the GOHT zone is operable to receive and convert the additional ADU fraction.

9. The system as in claim 1, further comprising:
    an olefins recovery train operable to receive and separate the mixed product stream into a fuel gas stream, an ethylene stream, a mixed C3s stream, and a mixed C4s stream, and
    a C4 distillation unit operable to receive and separate a portion of C4s recovered from the mixed product stream into an olefinic stream and a non-olefinic stream.

10. The system as in claim 9, wherein the MFSC zone is operable to receive and thermally crack the non-olefinic stream.

11. The system as in claim 9, further comprising a mixed butanols production zone operable to receive and convert a mixture of butenes from the C4 distillation unit into a mixed butanol product stream.

12. The system as in claim 9, wherein the naphtha hydrotreating zone is operable to produce a C5s stream, and further comprising a metathesis reaction zone operable to receive and convert all or a portion of the C5s stream into a propylene stream, and a C4/C5 raffinate stream, and wherein the MFSC zone is operable to receive and thermally crack the C4/C5 raffinate stream.

13. The system as in claim 9, wherein the naphtha hydrotreating zone is operable to produce a C5s stream, and further comprising a metathesis reaction zone operable to receive and convert all or a portion of the C5s stream into a propylene stream, and a C4/C5 raffinate stream; and a mixed butanols production zone operable to receive and convert a mixture of butenes from the C4 distillation unit into a mixed butanol product stream and an alkanes stream; wherein the MFSC zone is operable to receive and thermally crack the non-olefinic stream and the C4/C5 raffinate stream.

* * * * *